US008008020B2

(12) United States Patent
Fung et al.

(10) Patent No.: US 8,008,020 B2
(45) Date of Patent: Aug. 30, 2011

(54) BIOMARKERS FOR PERIPHERAL ARTERY DISEASE

(75) Inventors: Eric T. Fung, Los Altos, CA (US); John P. Cooke, Palo Alto, CA (US); Xiao-Ying Meng, Fremont, CA (US); Tai-Tung Yip, Cupertino, CA (US); Fujun Zhang, Fremont, CA (US)

(73) Assignees: Vermillion, Inc., Austin, TX (US); Board of Trustees of the Leland Stanford Junior University, Palo Alto, CA (US)

( * ) Notice: Subject to any disclaimer, the term of this patent is extended or adjusted under 35 U.S.C. 154(b) by 636 days.

(21) Appl. No.: 11/597,667

(22) PCT Filed: May 26, 2005

(86) PCT No.: PCT/US2005/018728
§ 371 (c)(1),
(2), (4) Date: Nov. 22, 2006

(87) PCT Pub. No.: WO2005/121758
PCT Pub. Date: Dec. 22, 2005

(65) Prior Publication Data
US 2008/0081342 A1 Apr. 3, 2008

Related U.S. Application Data

(60) Provisional application No. 60/577,348, filed on Jun. 3, 2004.

(51) Int. Cl.
*G01N 33/53* (2006.01)
(52) U.S. Cl. ............................ 435/7.1; 435/7.2; 436/518
(58) Field of Classification Search .................. None
See application file for complete search history.

(56) References Cited

U.S. PATENT DOCUMENTS

| 4,952,562 | A  | * | 8/1990  | Klein et al.     | 514/18   |
| 6,287,822 | B1 | * | 9/2001  | Gjerde et al.    | 435/91.2 |
| 6,306,591 | B1 | * | 10/2001 | Cockett et al.   | 435/6    |
| 6,475,796 | B1 | * | 11/2002 | Pollitt et al.   | 435/455  |
| 6,731,961 | B2 | * | 5/2004  | Braig et al.     | 600/310  |
| 7,622,306 | B2 | * | 11/2009 | Albitar et al.   | 436/173  |
| 2003/0096328 | A1 | * | 5/2003 | Smith et al.    | 435/7.23 |
| 2003/0125247 | A1 | * | 7/2003 | Rosen et al.    | 514/12   |
| 2004/0005566 | A1 | * | 1/2004 | DePhillipo et al. | 435/6  |
| 2005/0069518 | A1 | * | 3/2005 | Mousa et al.    | 424/78.3 |
| 2006/0240495 | A1 | * | 10/2006 | Buhimschi et al. | 435/7.92 |

OTHER PUBLICATIONS

Douglas et al. Functional significance of GP1b alpha receptor polymorphism in patients with coronary artery disease, European Heart Journal (2000) 21(supplement s):66 (P493).*
Gey et al. Management of peripheral arterial disease, American Family Physician (2000) 69:525-533.*
Ridker, Paul M. Clinical Application of C-Reactive Protein for Cardiovascular Disease Detection and Prevention, Circulation (2003) 107:363-369.*
Standl et al. Microalbuminuria in a random cohort of recently diagnosed Type 2 (non-insulin-dependent) diabetic patients living in the Great Munich Area, Diabetologia (1993) 36:1017-1020.*
O'Hare, A.M., et al.; "Cystatin C and incident peripheral arterial disease events in the elderly," 2005, *Arch. Intern. Med.*, vol. 165, pp. 2666-2670.
Nedelkov, D., et al.; "Design and use of multi-affinity surfaces in biomolecular interaction analysis-mass spectrometry (BIA/MS): a step toward the design of SPR/MS arrays," 2003, *Journal of Molecular Recognition*, vol. 16, pp. 15-19.
Saijo, Y., et al.; "Relationships of $\beta_2$-microglobulin to arterial stiffness in Japanese subjects," 2005, *Hypertens. Res.*, vol. 28, No. 6, pp. 505-511.
Schillinger, M., et al.; "Joint Effects of C-Reactive Protein and Glycated Hemoglobin in Predicting Future Cardiovascular Events of Patients With Advanced Atherosclerosis," 2003, *Circulation AHA Journals*, pp. 2323-2328 (November).
Standl, E., et al., "Predictors of 10-year macrovascular and overall mortality in patients with NIDDM: the Munich General Practioner Project," 1996, *Diabetologia*, vol. 39, pp. 1540-1545.
Thongboonkerd, V., et al.; "Proteomic analysis reveals alterations in the renal Kallikrein pathway during hypoxia-induced hypertension," 2002, *J. Biol. Chem.*, vol. 277, No. 33, pp. 34708-34716.
Tusher VG et al. "Significance analysis of microarrays applied to the ionizing radiation response." Proc Natl Acad Sci U S A. Apr. 24, 2001;98(9):5116-5121.

* cited by examiner

*Primary Examiner* — Jacob Cheu
(74) *Attorney, Agent, or Firm* — Edwards Angell Palmer & Dodge LLP; Peter F. Corless; Melissa Hunter-Ensor, Esq.

(57) ABSTRACT

This invention provides biomarkers whose concentrations in blood plasma are associated with the presence or absence of PAD in the patient from whom the plasma sample is taken. The invention also provides biomarkers for distinguishing between PAD patients who are long claudicators and PAD patients who are not. In addition, the invention provides methods for identifying additional biomarkers, methods for detecting the biomarkers in patients, and methods for identifying agents, including pharmaceutical agents, which interact with the biomarkers and are useful for preventing or treating PAD in patients.

18 Claims, 22 Drawing Sheets

BIOMARKERS FOR PERIPHERAL ARTERY DISEASE

FEDERALLY-SPONSORED RESEARCH OR DEVELOPMENT

This invention was made with Government support under contract HL063685 awarded by the National Institutes of Health. The Government has certain rights in this invention.

BACKGROUND OF THE INVENTION

Atherosclerosis is the accumulation of lipid-fibrin plaques on the luminal wall of vascular endothelial cells. The presence of atherosclerotic plaques can severely diminish vascular flow to target organs, leading to morbidity and mortality. The distribution of atherosclerotic plaques is broadly divided into the coronary arteries and the peripheral circulation (most commonly, the lower extremities). Some individuals are primarily affected in the coronary arteries (causing coronary artery disease, "CAD"), in the peripheral arteries (causing peripheral artery disease, "PAD"), while other individuals are substantially affected in both regions. Risk factors for PAD include smoking, hyperlipidemia, hypertension, diabetes, and family history. Untreated PAD can lead to decreased mobility, ulcers, gangrene, and may ultimately require amputation of the affected extremity.

Because of compensatory mechanisms that exist in normal physiologic responses, clinical symptoms from CAD and PAD may not present themselves until the disease has progressed to severe levels. No effective screening tests exist. Both CAD and PAD can be quantified using invasive techniques such as angiography. PAD may be quantitated using a Doppler ultrasound to measure the ankle-brachial index ("ABI"), which entails calculating the ratio of the systolic reading of the pressure in the upper extremity versus the lower extremity. In most healthy individuals, the ratio is close to 1 (i.e., 0.90 or greater) while in patients with a ratio less than 0.90, PAD is diagnosed. Generally, the lower the ratio, the more severe the disease.

The measurement of the ankle-brachial index is not generally practiced, leading to the under-diagnosis of PAD. Moreover, in patients with diabetes, who constitute greater than 20% of patients with PAD, poor vascular compressibility may cause the ABI test to yield false negatives. Furthermore, ABI does not accurately distinguish PAD patients from long claudicator ("LC") PAD patients who may have somewhat milder forms of PAD, at least as measured by the decreased pain experienced by LC patients during and after exercise. PAD, when diagnosed early, is amenable to treatments which slow progression of the disease. Therefore, a need exists for improved tools which efficiently and accurately diagnose PAD. In particular, a blood test for PAD would be helpful since it could be performed in a routine clinical setting.

SUMMARY OF THE INVENTION

This invention provides biomarkers whose concentrations in blood plasma are associated with the presence or absence of PAD in the patient from whom the plasma sample is taken. The invention also provides biomarkers for distinguishing between PAD patients who are long claudicators and PAD patients who are not. In addition, the invention provides methods for identifying additional biomarkers, methods for detecting the biomarkers in patients, and methods for identifying agents, including pharmaceutical agents, which interact with the biomarkers and are useful for preventing or treating PAD in patients.

Although this invention describes biomarkers that have been specifically associated with PAD, these markers may also be associated with CAD, since PAD shares many pathophysiologic and clinical features with CAD.

The present invention provides polypeptide-based biomarkers that are differentially present in subjects having PAD and, in particular, PAD versus normal subjects. In addition, the present invention provides methods of using the polypeptide-based biomarkers to qualify disease in a subject.

As such, in one aspect, the present invention provides a method for qualifying PAD status in a subject, the method comprising: (a) measuring at least one biomarker in a biological sample from the subject, wherein the at least one biomarker is selected from the group consisting of the biomarkers of Tables 1A, 1B, 2, 3, 4, 5, 6 and 18, described herein; and (b) correlating the measurement with PAD status. In one embodiment, the sample is blood plasma. In a preferred embodiment, the biomarkers are selected from Table 1A or 1B. In a more preferred embodiment, the biomarkers are selected from table 1A. In another preferred embodiment, the biomarkers are selected from the group consisting of albumin, fetuin, triple charge dimer of albumin, transthyretin, α1B glycoprotein and dimer of α1-antitrypsin. In a related embodiment, each of the biomarkers selected from the group albumin, fetuin, triple charge dimer of albumin, transthyretin, α1B glycoprotein and dimer of α1-antitrypsin are measured. In yet another related embodiment, the biomarkers are selected from the group consisting of biomarkers listed in Table 18, described herein.

In another embodiment, the biological samples described above are taken from subjects before, immediately after, and two hours after exercise. In a preferred embodiment, the exercise is a treadmill exercise lasting approximately fifteen minutes.

In yet another embodiment, the measurements of biomarkers in samples taken immediately after exercise are measurements of biomarkers from the group listed in Table 2. In a related embodiment, measurements are preferably taken of biomarkers from the group consisting of kappa chain of IgG, transthyretin and M23651.9. In a related embodiment, each of those three biomarkers are measured.

In yet another embodiment, the measurements of biomarkers in samples taken two hours after exercise are measurements of biomarkers from the group listed in Table 3. In a preferred embodiment, the measurements of biomarkers in samples taken two hours after exercise are measurements of biomarkers from the group consisting of M75053.2, M18183.9 and M11950.4. In a related embodiment, each of these biomarkers is measured.

In yet another embodiment, samples are taken from a subject before, immediately after, and two hours after exercise and biomarkers from Tables 1, 2 and 3, respectively, are measured in each of the samples.

In another embodiment, the invention provides a method for qualifying PAD status in a subject comprising measuring a biomarker from Tables 4, 5 or 6, wherein the biomarker is measured in at least two samples taken from a subject, one of which is taken from the subject immediately or two hours following exercise.

In yet another embodiment, the subject from whom the samples are obtained is at risk for PAD. In a related embodiment, the subject at risk for PAD smokes cigarettes, has hyperlipidemia, has hypertension, diabetes, or belongs to a family with a history of peripheral artery disease.

The invention also provides a fit comprising: a solid support comprising at least one capture reagent attached thereto, wherein the capture reagents bind at least one biomarker selected from the group consisting of the biomarkers of Tables 1A, 1B, 2, 3, 4, 5, 6 and 18; and a container containing at least one of the biomarkers.

Other preferred embodiments are described elsewhere herein and in the Claims. Additional features, objects and advantages of the invention and its preferred embodiments will become apparent from the detailed description, examples and claims that follow.

DETAILED DESCRIPTION OF THE INVENTION AND PREFERRED EMBODIMENTS

I. Introduction

Figure 1A:
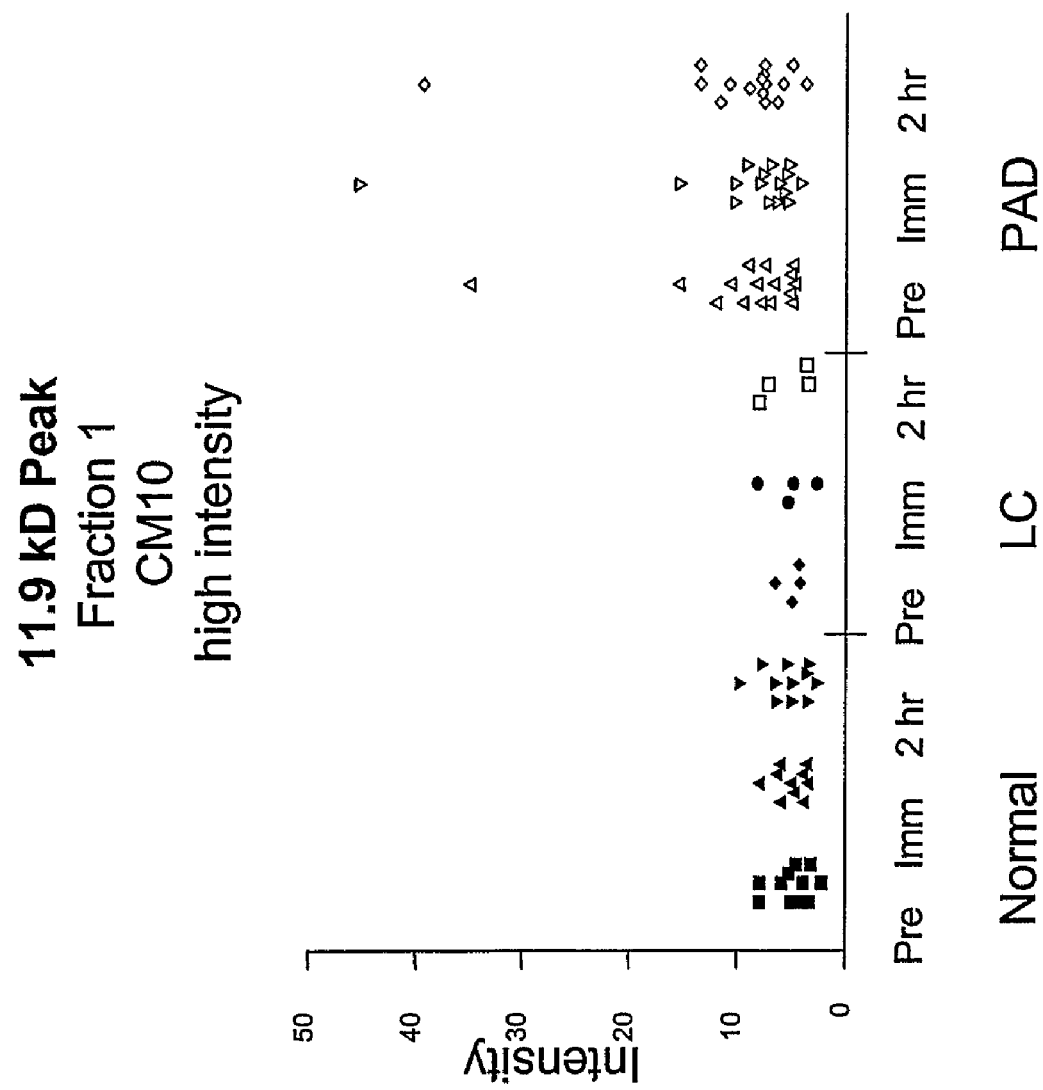
FIGS. 1A-1U show graphs which illustrate the distribution of measured intensities for biomarker peaks judged to be significant by either the Kruskal-Wallis or Significant Analysis of Microarray tests, as described herein. Each graph is described by the Q Hyper DF fraction in which the biomarker appears, the array on which the biomarker was observed (IMAC30 or CM10 arrays), and the beam intensity (high or low) used to visualize the biomarker. The Y-axis is peak intensity. The X-axis is divided into three sectors corresponding to Normal patients, PAD long claudicators ("LC") and PAD patients who are not long claudicators ("PAD"). Each sector is further divided into the three time points at which blood plasma samples were obtained from patients: "pre" (before treadmill exercise); "imm" (immediately after treadmill exercise); and "2 hr" (two hours after treadmill exercise).
Figure 1B:
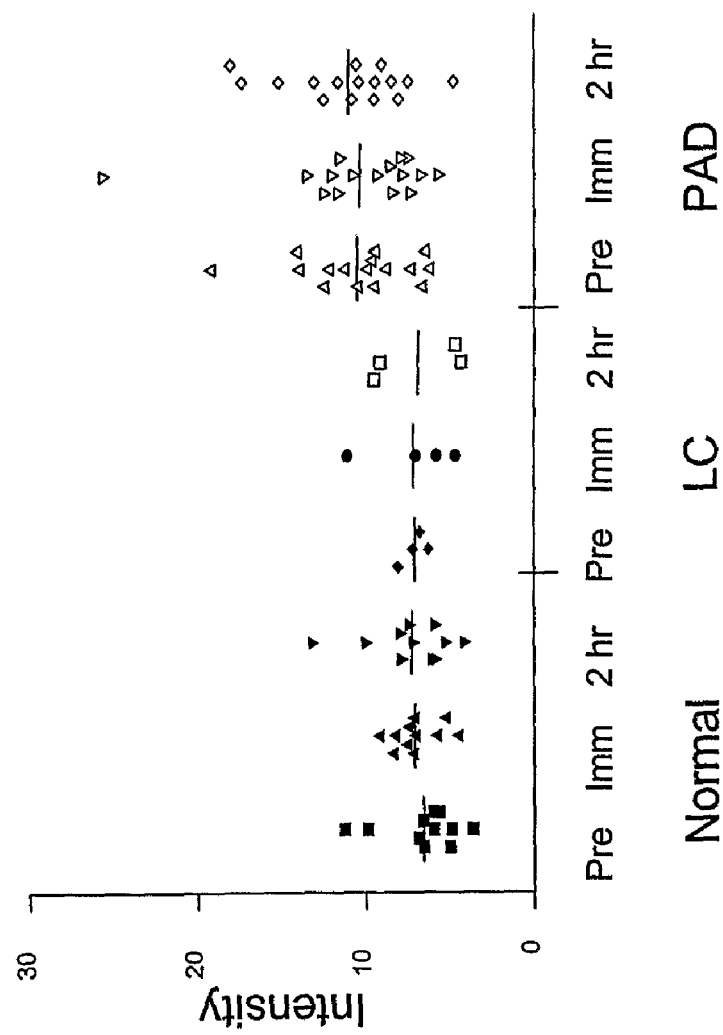
Figure 1C:
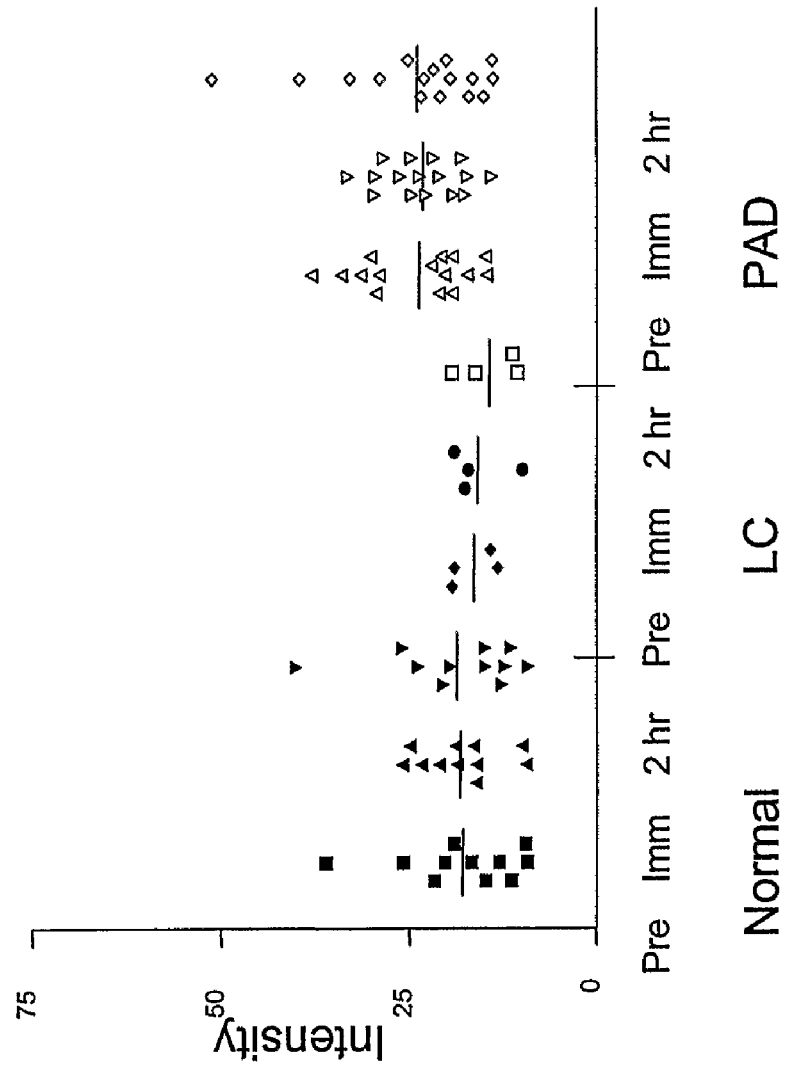
Figure 1D:
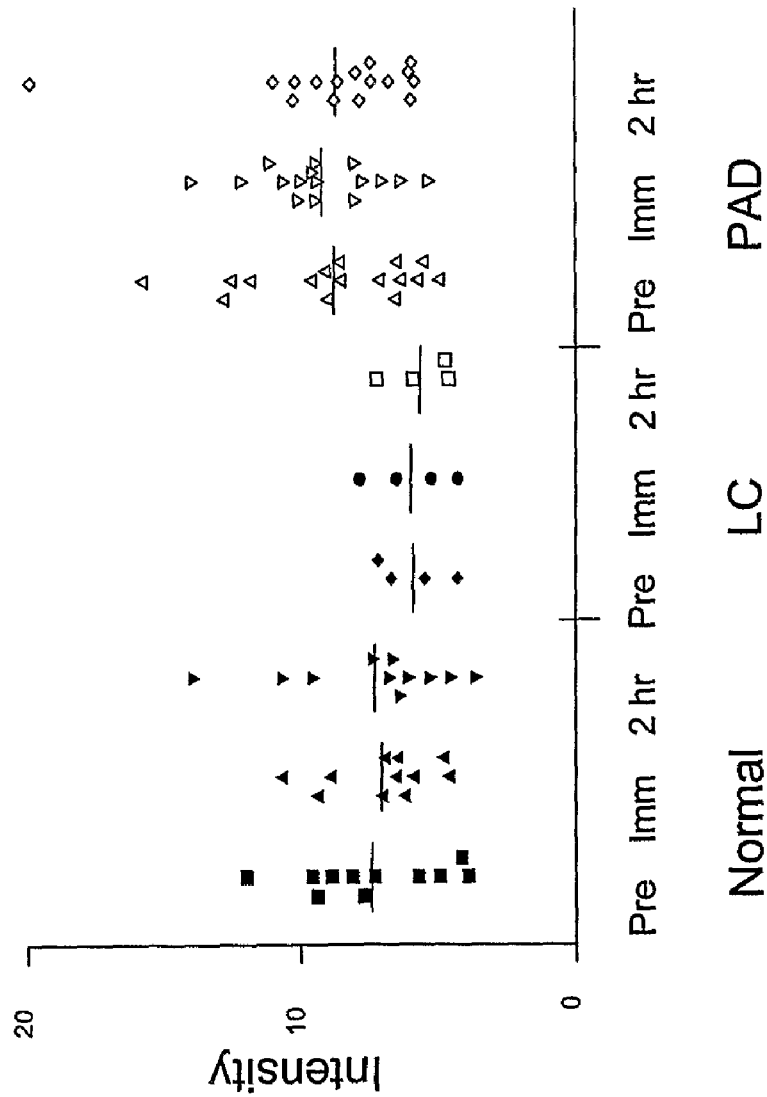
Figure 1E:
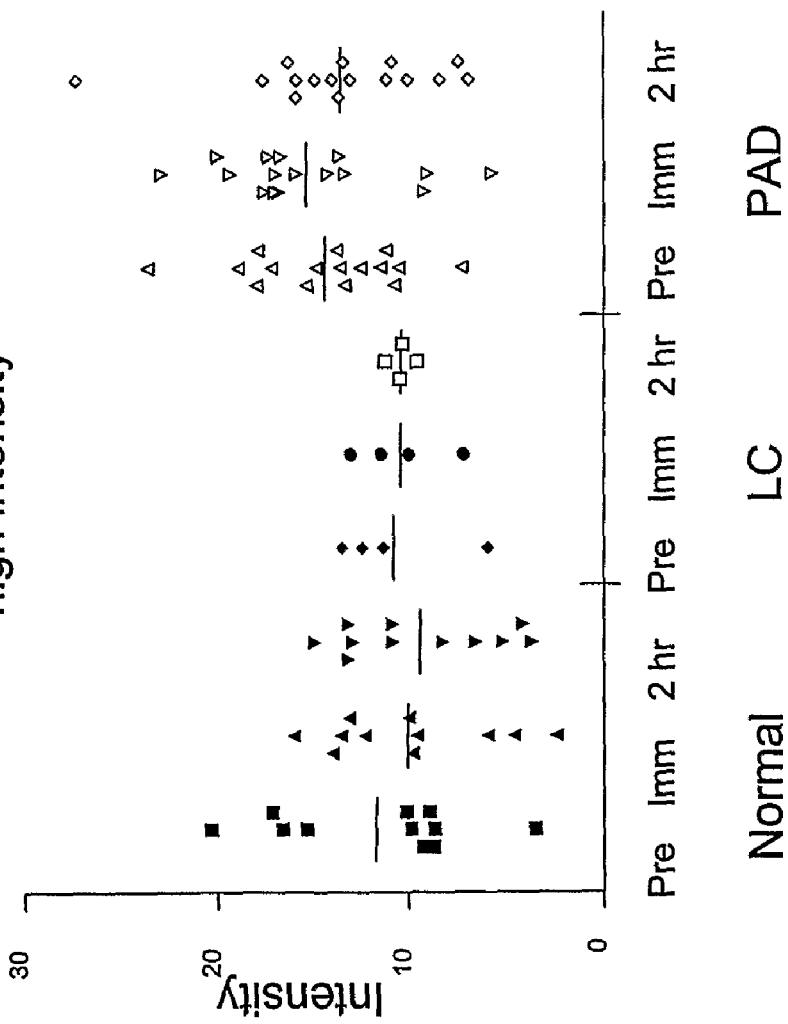
Figure 1F:
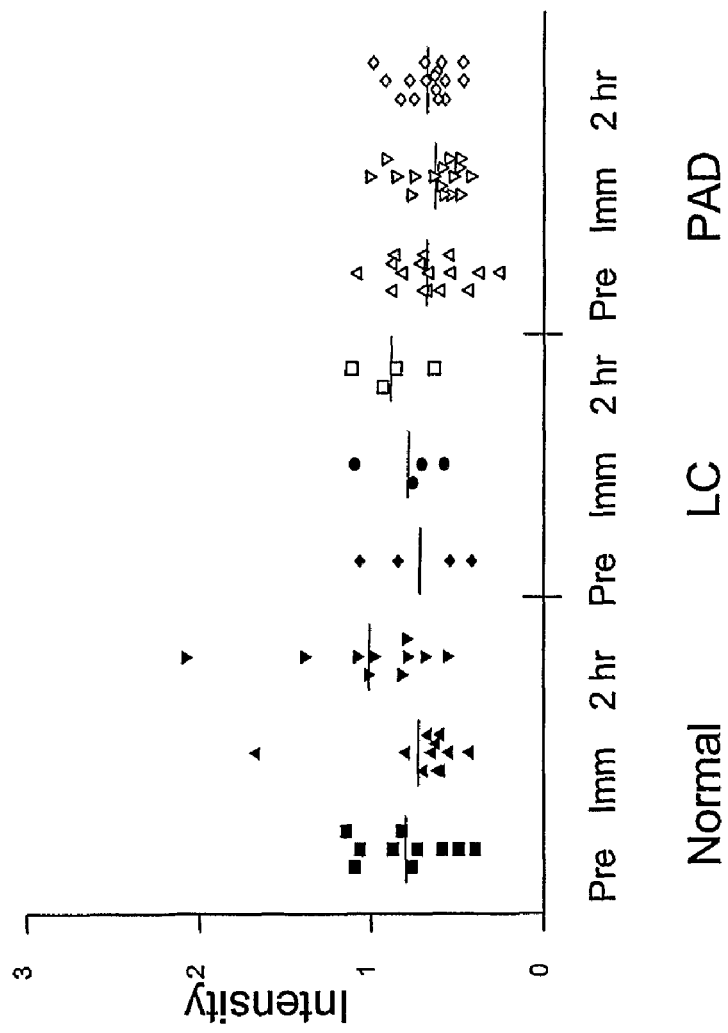
Figure 1G:
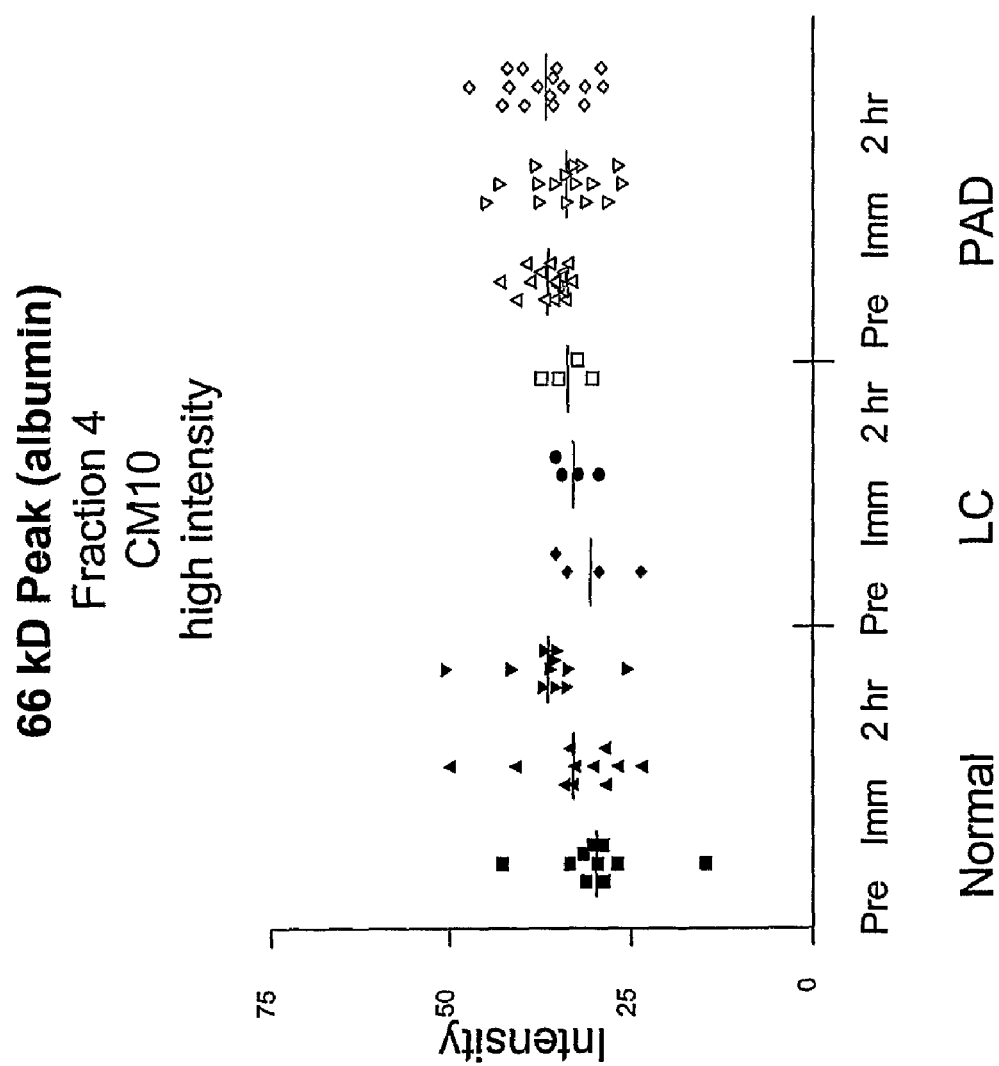
Figure 1H:
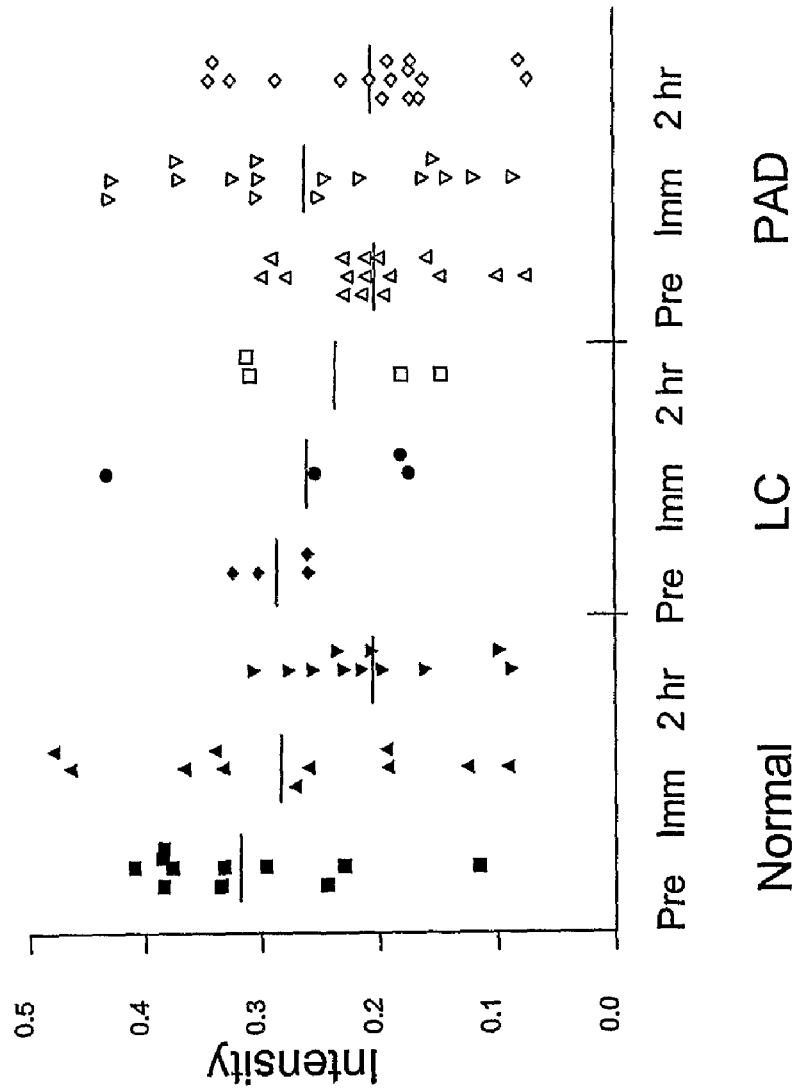
Figure 1I:
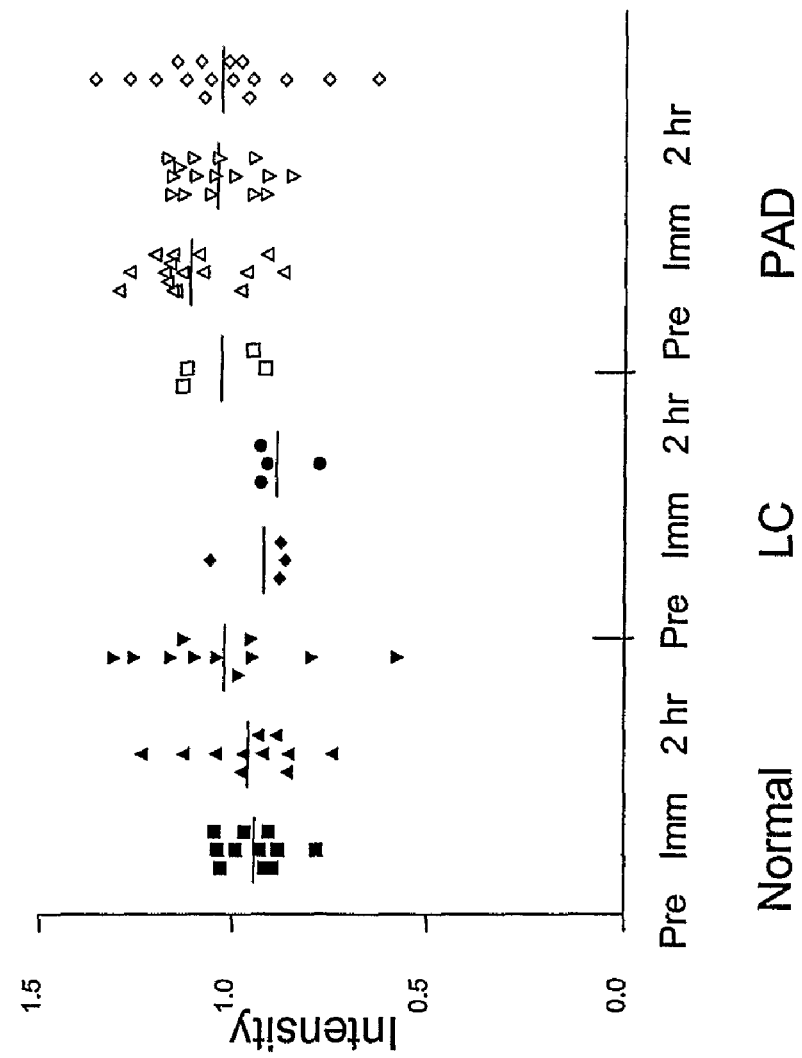
Figure 1J:
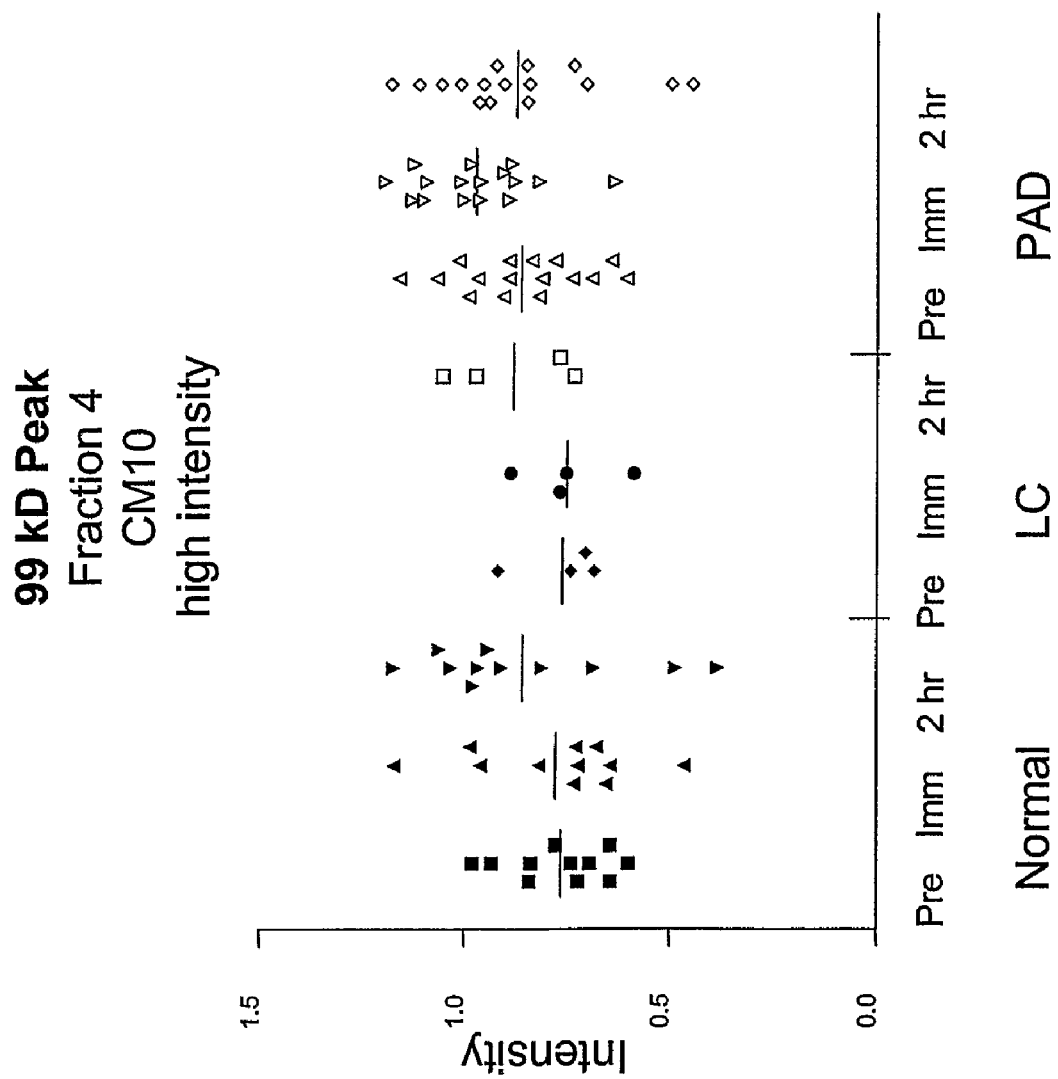
Figure 1K:
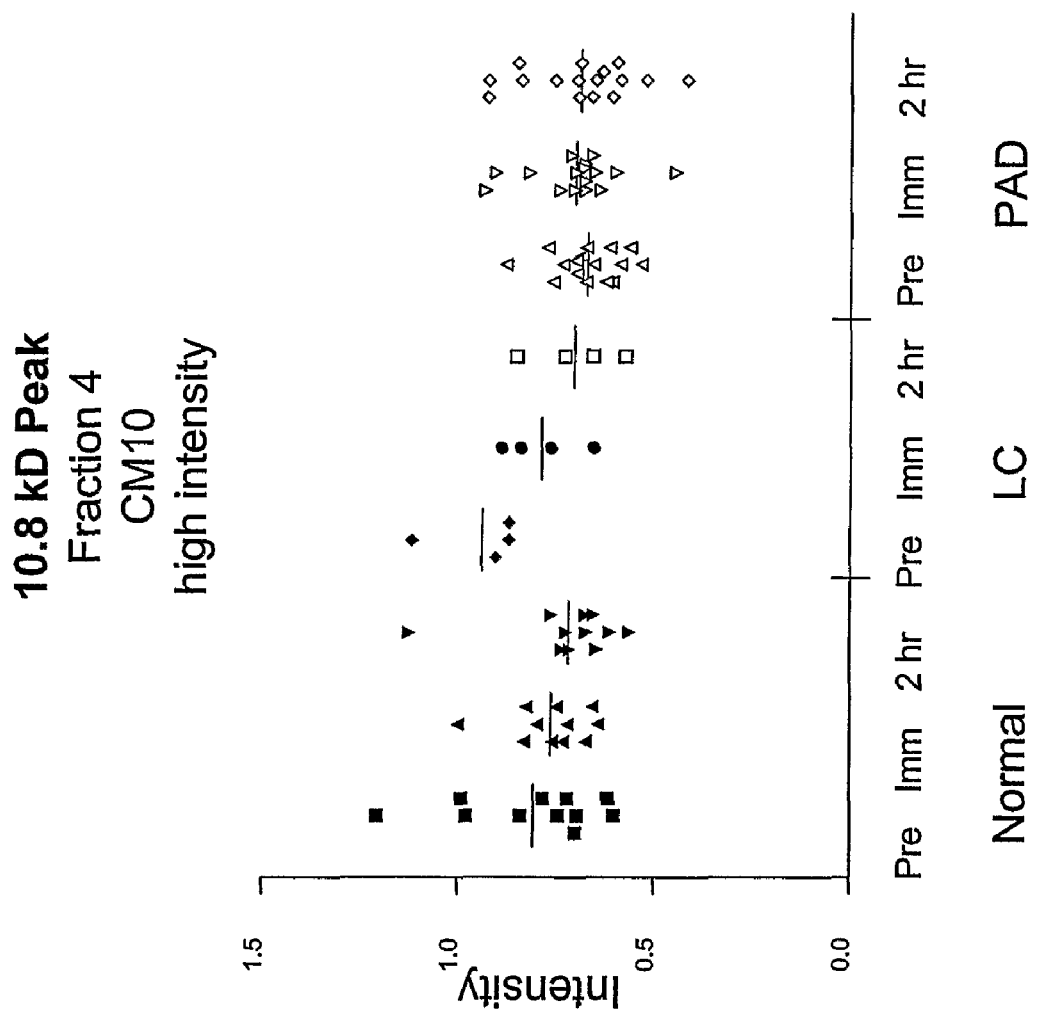
Figure 1L:
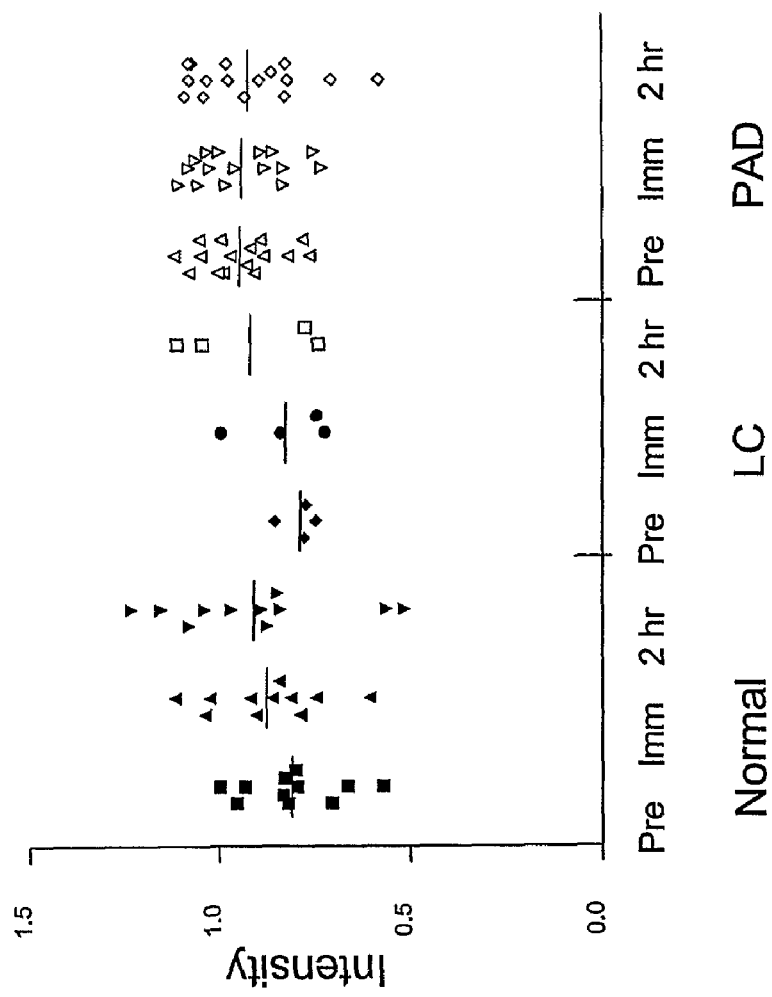
Figure 1M:
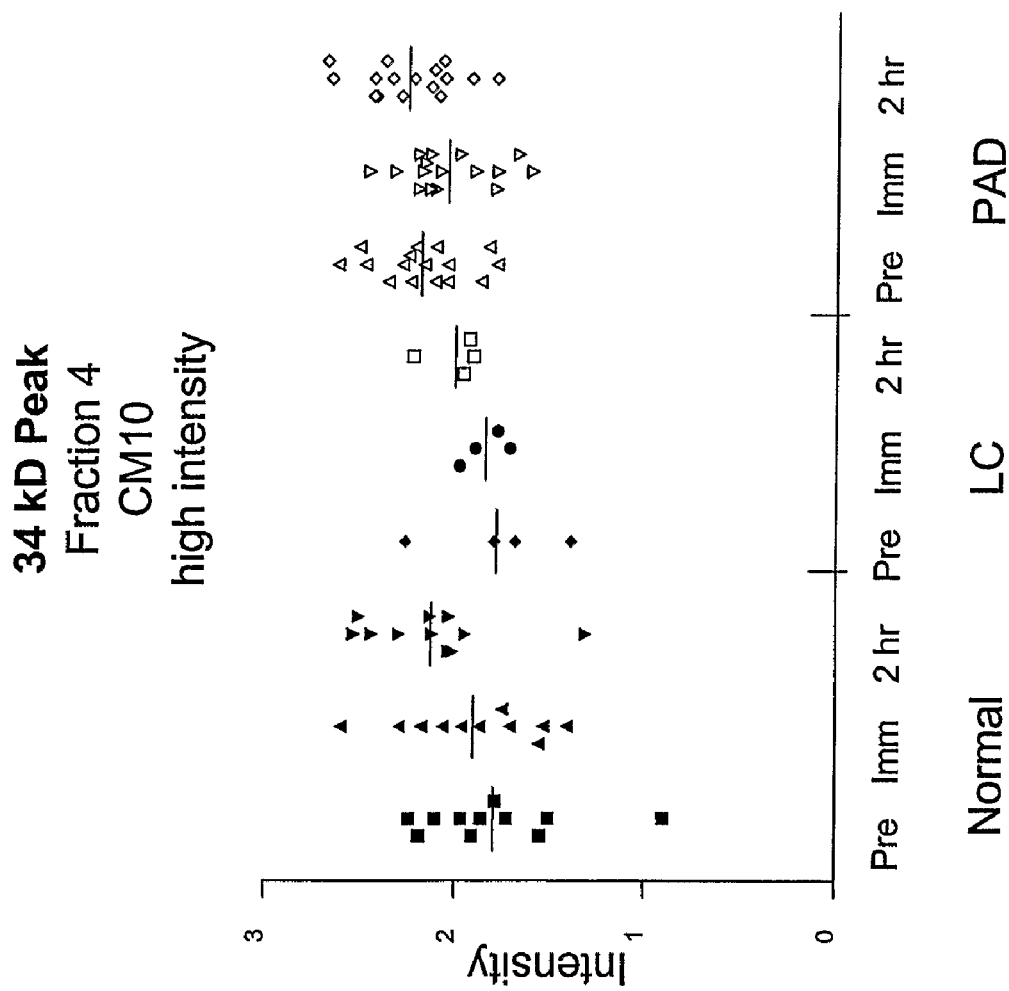
Figure 1N:
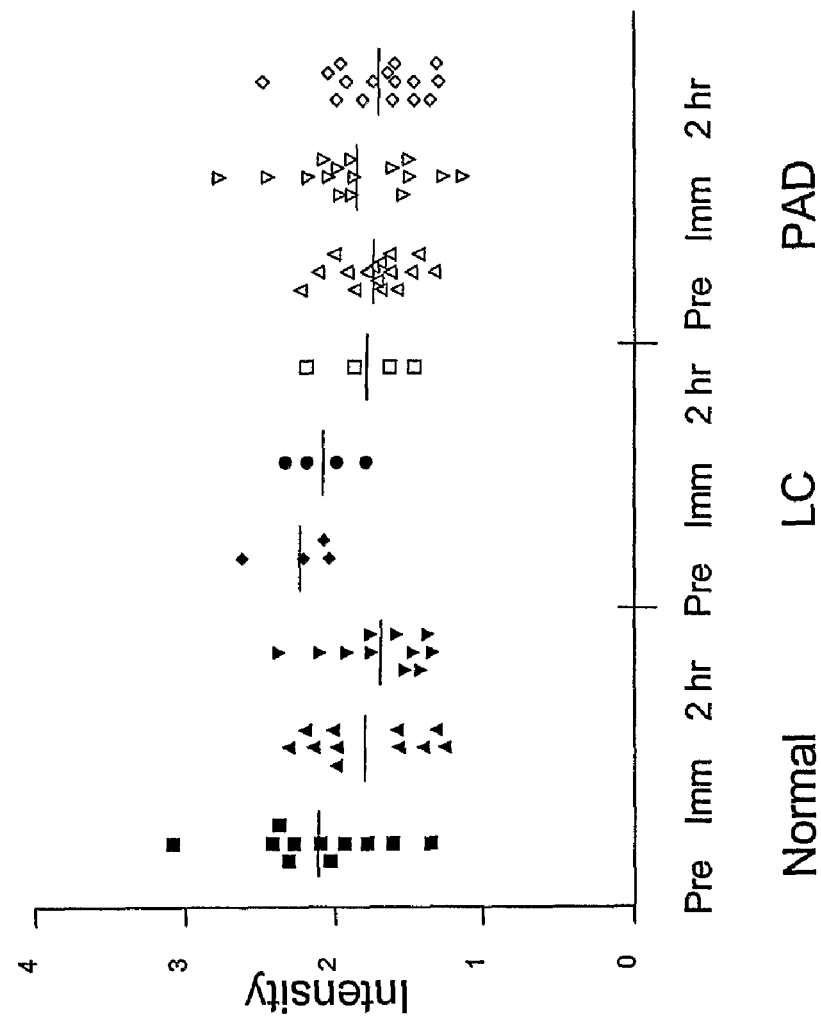
Figure 10:
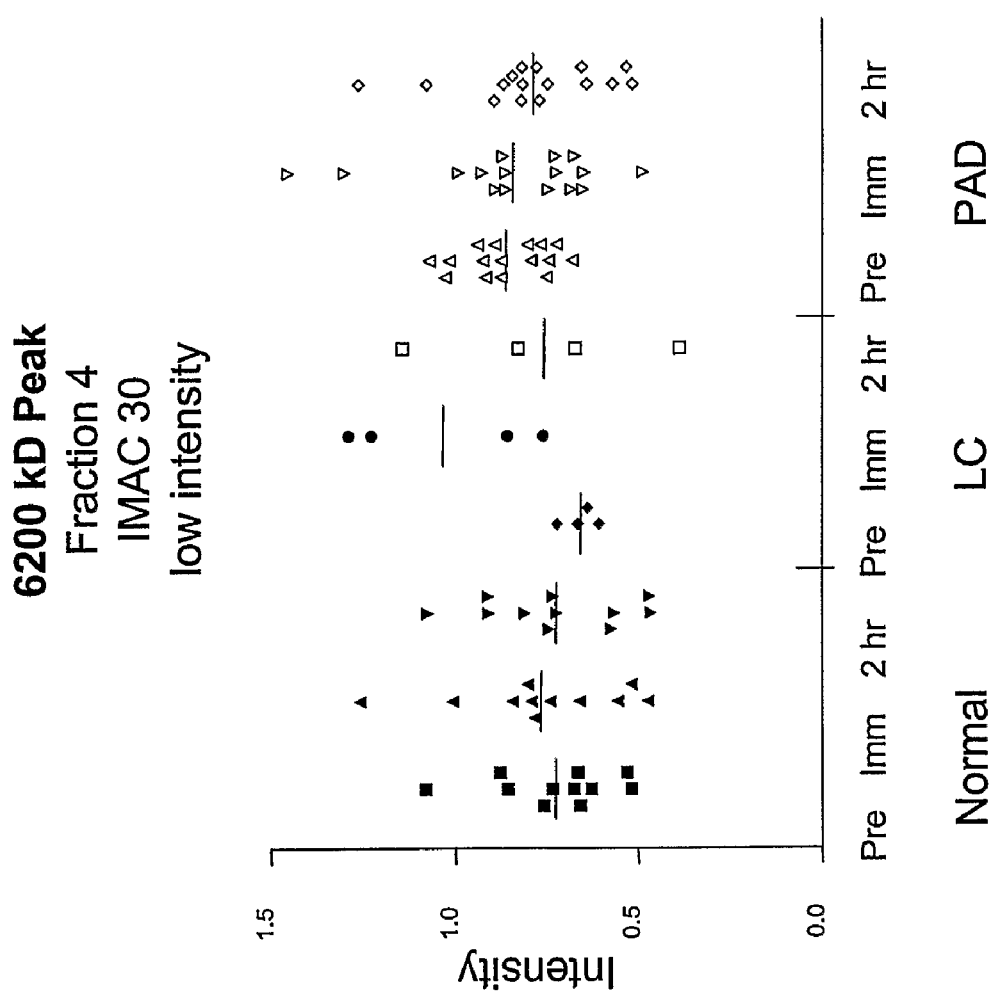
Figure 1P:
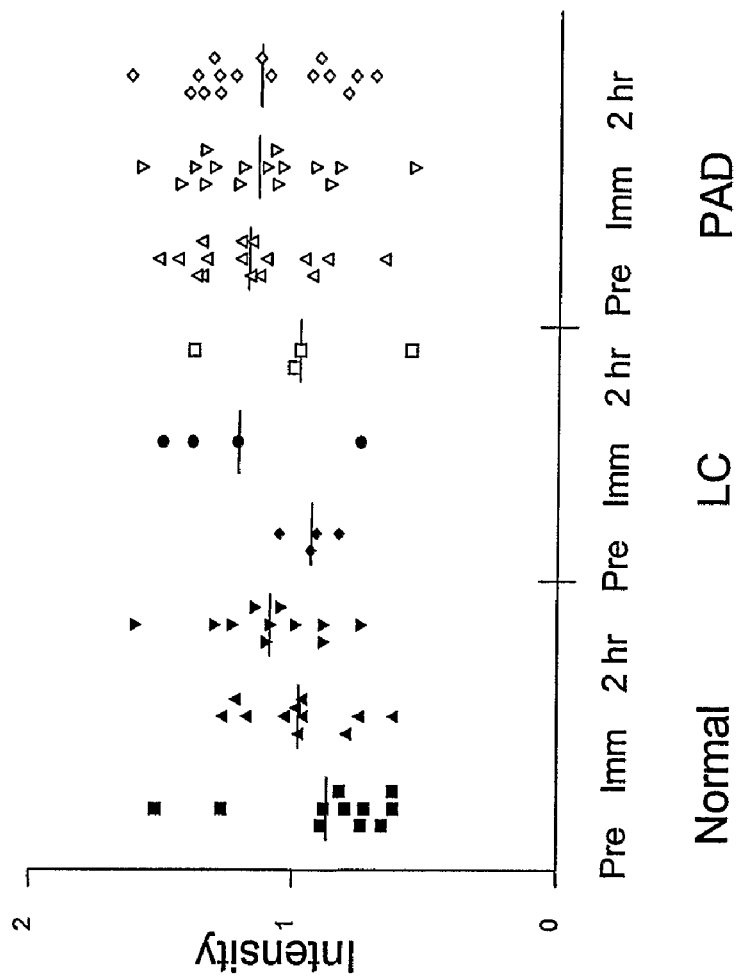
Figure 1Q:
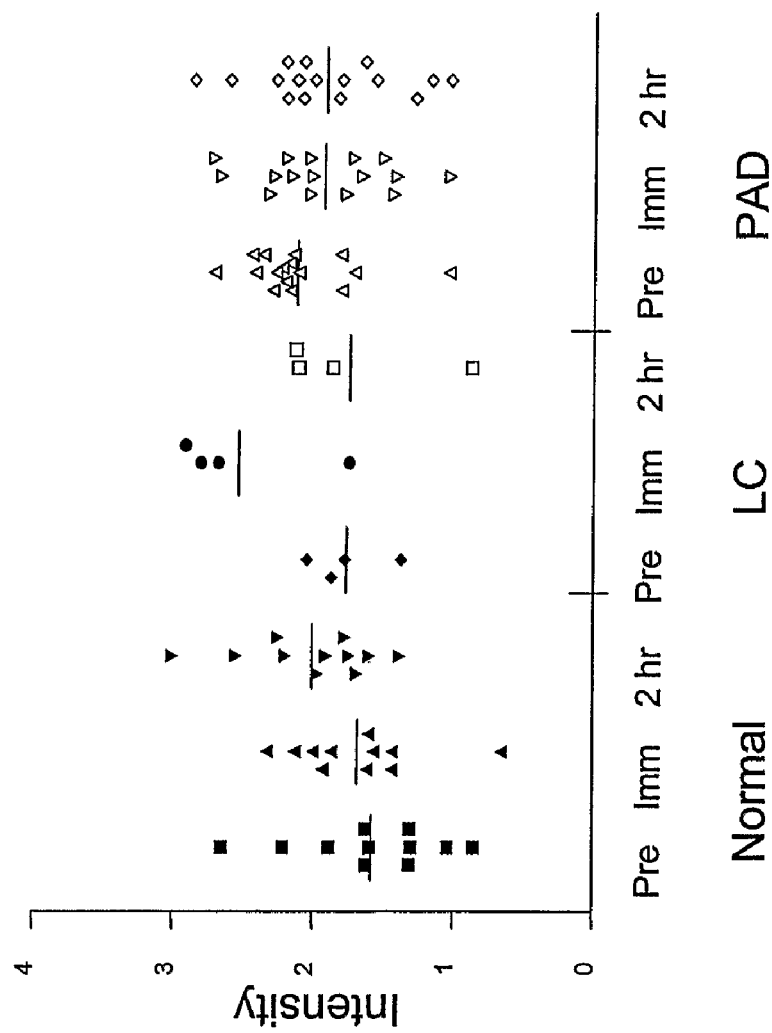
Figure 1R:
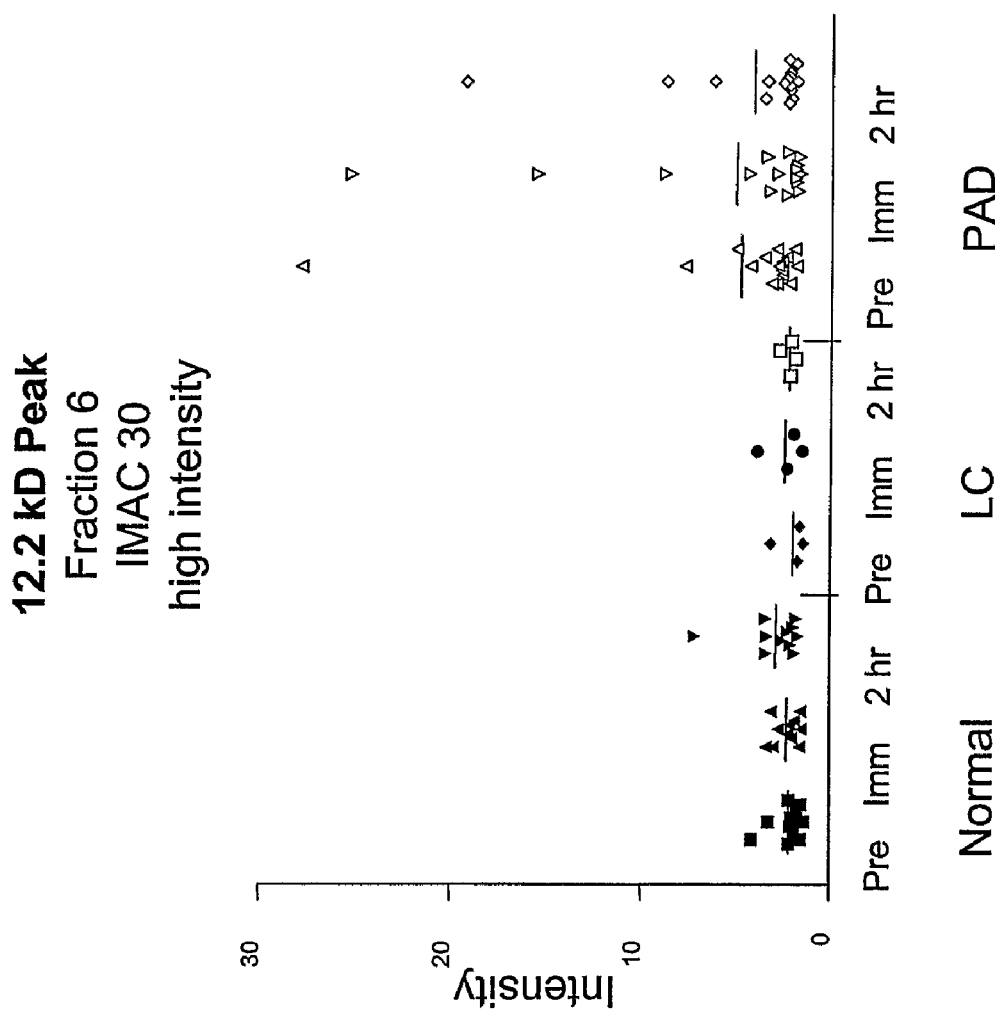
Figure 1S:
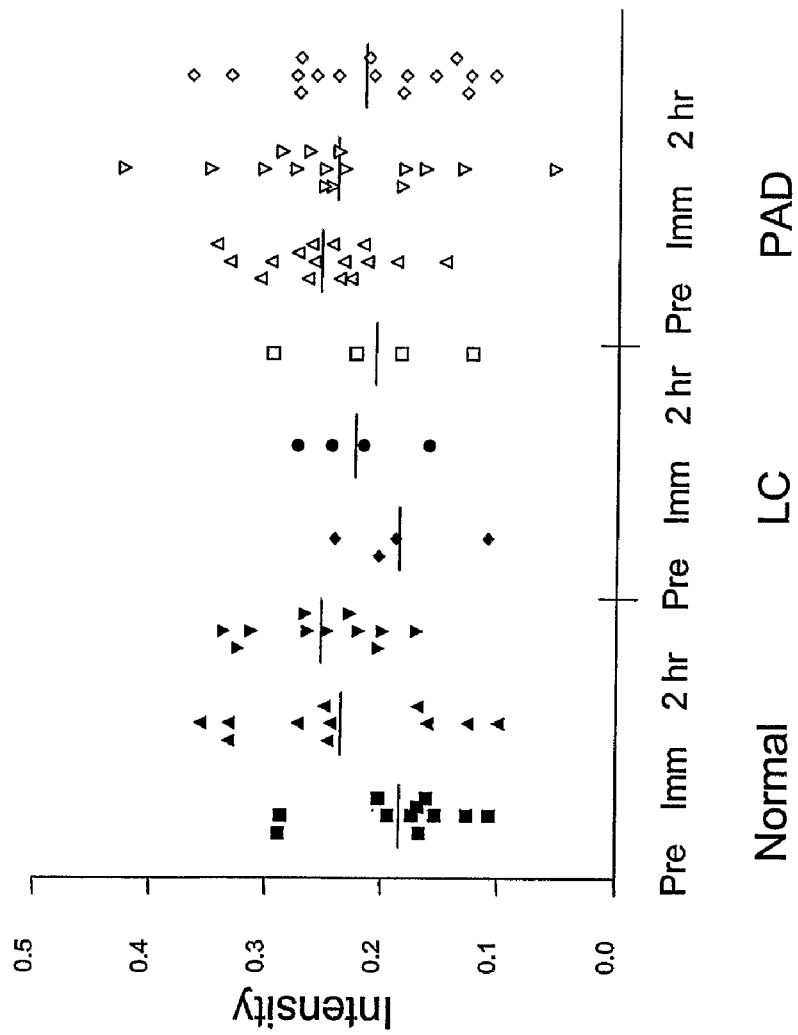
Figure 1T:
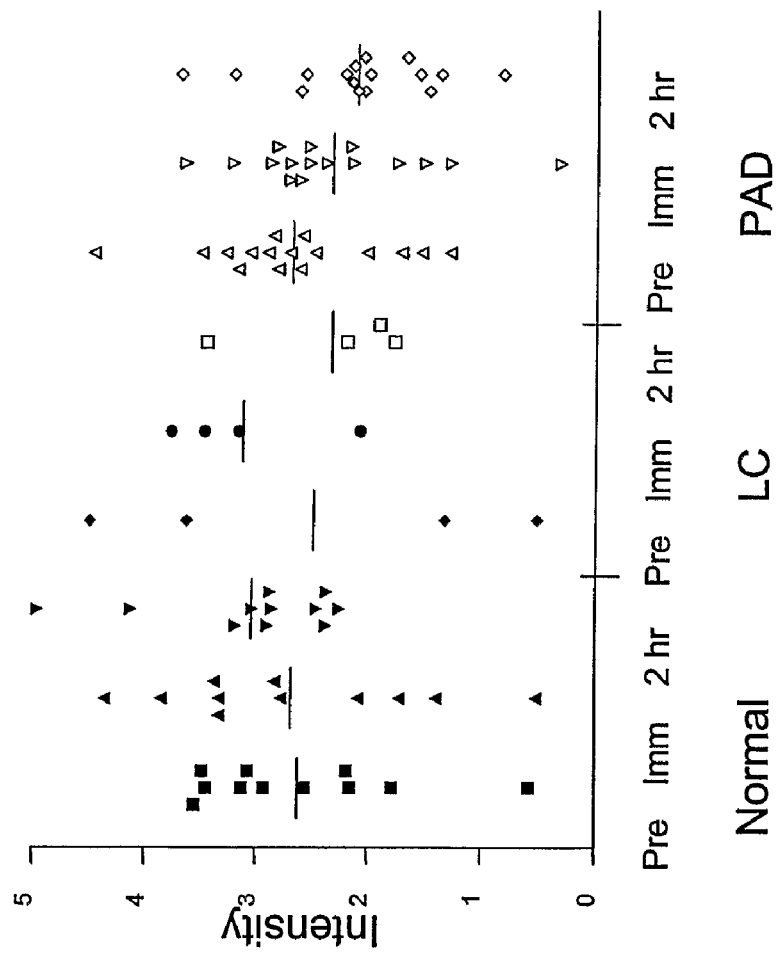
Figure 1U:
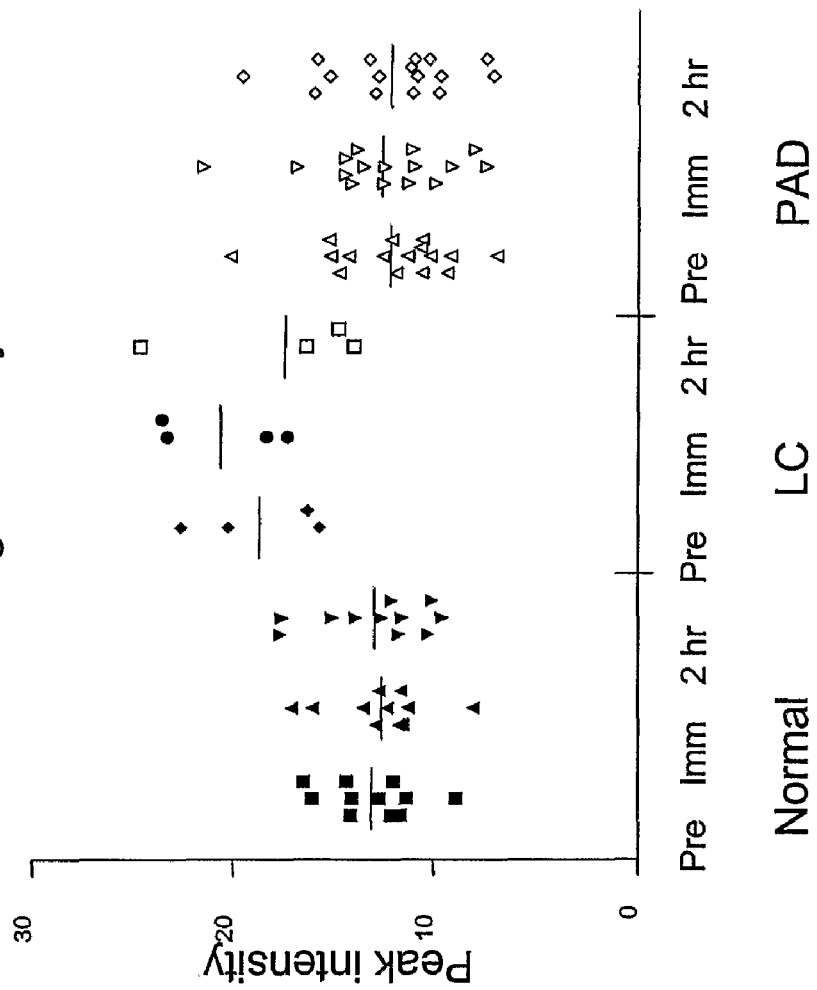

A biomarker is an organic biomolecule which is differentially present in a sample taken from a subject of one phenotypic status (e.g., having a disease such as PAD) as compared with another phenotypic status (e.g., a normal undiseased patient). A biomarker is differentially present between different phenotypic statuses if the mean or median expression level of the biomarker in the different groups is calculated to be statistically significant. Common tests for statistical significance include, among others, t-test, ANOVA, Kruskal-Wallis, Wilcoxon, Mann-Whitney, Significance Analysis of Microarrays, and odds ratio. Biomarkers, alone or in combination, provide measures of relative risk that a subject belongs to one phenotypic status or another. Therefore, they are useful as markers for disease (diagnostics), therapeutic effectiveness of a drug (theranostics) and drug toxicity.

II. Identification of Biomarkers for PAD

A. Study Design

This invention provides polypeptide-based biomarkers that are differentially present in subjects having PAD versus subjects who are normal (i.e., subjects not afflicted by PAD). They are characterized by mass-to-charge ratio as determined by mass spectrometry, by the shape of their spectral peak in time-of-flight mass spectrometry and by their binding characteristics to adsorbent surfaces. These characteristics provide one method to determine whether a particular detected biomolecule is a biomarker of this invention. Because these characteristics reflect inherent characteristics of the biomolecules, the biomolecules may be discriminated using other processes. In one aspect, this invention provides these biomarkers in isolated form.

The biomarkers were discovered using SELDI technology employing ProteinChip arrays from Ciphergen Biosystems, Inc. (Fremont, Calif.) ("Ciphergen"). The study set consisted of 20 patients with PAD and 11 age-matched controls. Subjects placed in the PAD group were those with an ankle-brachial index of 0.9 or less. All subjects underwent a treadmill test according to the Skinner-Gardner protocol (Gardner AW et al., *Med Sci Sports Exerc.*, 24:163-170 (1992)). Briefly, subjects were asked to walk on a flat treadmill operating at 2 miles per hour. The speed of the treadmill was increased 2% every two minutes. Subjects were instructed to indicate when leg claudication began and then to walk as long as they could endure the pain. Four of the 20 patients with PAD were defined to be long claudicators ("LC") due to an absolute claudication time of greater than 12 minutes, i.e., LC subjects were able to endure for longer periods, relative to other members of the PAD group, the pain induced by walking.

For each participant in each group, three plasma samples were analyzed for each participant: a baseline sample (before exercise), a sample taken immediately after an exercise treadmill test, and a third sample taken 2 hours after the exercise treadmill test. Therefore, 93 plasma samples were analyzed in total. Each plasma sample was subjected to fractionation on a QhyperDF column. After fractionation, selected fractions were analyzed using Ciphergen's IMAC30 or CM10 ProteinChips, as described herein. The spectra of polypeptides in the samples were generated by time-of-flight mass spectrometry on a Ciphergen PBSII mass spectrometer. The spectra thus obtained were analyzed by Ciphergen Express™ Data Manager Software with Biomarker Wizard and Biomarker Pattern Software from Ciphergen Biosystems, Inc.

B. Biomarker Detection Using Study Samples

A preferred protocol for the detection of the biomarkers of this invention is as follows. Preferably, the biological sample to be tested, e.g., blood plasma, is subject to pre-fractionation before SELDI analysis. This simplifies the sample and improves sensitivity. A preferred method of pre-fractionation involves contacting the sample with an anion exchange chromatographic material, such as Q HyperD (BioSepra, SA) or C4 silica gel. The bound materials are then subject to stepwise pH elution using buffers at pH 9, pH 7, pH 5 and pH 4 (see the detailed protocol in the Materials and Methods section, below) The fractions in which the biomarkers are eluted are indicated in the Tables and FIG. 1. The fractions containing the biomarker are collected.

The pre-fractionated sample is then contacted with an affinity capture probe comprising a hydrophilic adsorbent (preferably a NP20 ProteinChip array (Ciphergen Biosystems, Inc.)) or a metal chelate (e.g., an IMAC) adsorbent (preferably an IMAC30 ProteinChip array (Ciphergen Biosystems, Inc.)) or a cation exchange adsorbent (preferably a CM10 ProteinChip array (Ciphergen Biosystems, Inc.)). The probe is washed with a buffer that will retain the biomarker while washing away unbound molecules. For example, a suitable wash for IMAC30 chips includes, but is not limited to, 50 mM Tris pH 8.0 supplemented with 500 mM NaCl. For NP20 ProteinChips, a suitable wash buffer includes, but is not limited to, 5 mM Hepes pH 7.0 and deionized water. For CM10 ProteinChips, a suitable wash includes, but is not limited to, 100 mM ammonium acetate pH 4.0. The biomarkers are detected by laser desorption/ionization mass spectrometry.

Alternatively, if antibodies that recognize the biomarker are available, these antibodies can be attached to the surface of a probe, such as a pre-activated PS10 or PS20 ProteinChip array (Ciphergen Biosystems, Inc.). The antibodies can capture the biomarkers from a sample onto the probe surface. Then the biomarkers can be detected by, e.g., laser desorption/ionization mass spectrometry. Similarly, antibodies to proteins whose in vivo concentrations or activity have previously been observed to change in PAD patients relative to normal subjects may also be attached to a probe surface. Such antibodies include C-reactive protein, serum albumin, or apolipoprotein A1.

As described in the Examples, univariate analysis was performed using the Kruskal-Wallis test to compare peak intensities at a particular time point across all three groups: (1) control or "normal" subjects; (2) subjects with PAD, and (3) subjects with PAD who are also long claudicators ("long claudicator PAD"). The Kruskal-Wallis test was used to compare all three patient groups at a given time point (e.g., baseline (before exercise), immediately after exercise, or 2 hours after exercise, as defined above). For example, a p value of 0.05 or lower obtained with the Kruskal-Wallis test for a particular biomarker indicates that, at a given time point (e.g., before exercise), on a given chip (e.g., an IMAC30 chip), the biomarker may be found in a particular fraction (e.g., fraction 4 of on a QHyper DF column) at significantly higher or lower concentration in one patient group relative to another.

The Kruskal-Wallis test was also used to analyze peak differences over time within each patient group. In this analysis, a p value of 0.05 or lower obtained with the Kruskal-Wallis test for a particular biomarker indicates that, for a particular patient status (e.g., a subject with PAD), on a given chip (e.g., an IMAC30 chip), the biomarker may be found in a particular fraction (e.g., fraction 4 of on a QHyper DF column) at a significantly higher or lower concentration at one point time point relative to another (e.g., the intensity of a peak associated with the biomarker may increase significantly 2 hours after exercise relative to pre-exercise).

The Mann-Whitney test was also used to directly compare peaks observed in two groups at a particular time point, or when directly comparing peaks observed at two time points within a particular group.

Finally, the Significance Analysis for Microarrays software ("SAM") was used to identify significant peaks. SAM is described in detail in Tusher V, et al., *Proc. Natl. Acad. Sci.*, 98: 5116-5124 (2001).

The Tables provided herein list the biomarkers whose concentration changes significantly (i.e., $p \leq 0.05$) between patient groups or between time points within patient groups, as determined using the aforementioned tests. For each biomarker, the Tables indicate the mass to charge (m/z) ratio, the p value, the array type, the beam intensity (high or low), the fraction from the profiling column where the biomarker is found and whether the relative average peak intensity for each peak is up or down-regulated relative to the average intensity read for the biomarker in the control sample (e.g., a non-PAD subject or a subject before exercise). The m/z value is the average reading for that particular peak. For example, Table 1B compiles particularly significant peaks observed at the pre-exercise time point (p values<0.05). The approximately 5.487 kD peak observed at the pre-exercise time point in fraction 1 on the IMAC30 chip, read at low energy, has a p value of approximately 0.013. By reference to Table 7, the average intensities observed for this peak were 16.9 in the normal pre-exercise group, 26.7 in the long claudicator (LC) group, and 11.3 in the PAD group.

Tables 1-3 compile biomarkers and conditions for which peaks with significant intensities may be observed, where the significance is determined by a Kruskal-Wallis analysis of peak differences between three patient groups (i.e., normal, long claudicator PAD, and PAD) at specified time points. Specifically, Table 1A compiles the biomarkers with p values<0.01 which may be used to qualify PAD status at the pre-exercise (baseline) time point. Similarly, Table 1B compiles the biomarkers with p values<0.05 which may be correlated with PAD status at the pre-exercise (baseline) time point. Table 2 compiles the biomarkers with preferred p values<0.01 as well as those biomarkers with p values<0.05 which may be used to qualify PAD status using samples taken from patients immediately after the patients have completed a treadmill exercise. Table 3 compiles the biomarkers with preferred p values<0.01 as well as those biomarkers with p values<0.05 which may be used to qualify PAD status using samples taken from patients approximately 2 hours after a treadmill exercise.

As with Tables 1-3, Tables 4-6 also compile biomarkers and conditions for which peaks with significant intensities may be observed, where the significance is determined by a Kruskal-Wallis analysis of peak differences between time points within a patient group. The biomarkers in Tables 4-6 are those whose concentration in blood plasma changes significantly immediately after a treadmill exercise or two hours after a treadmill exercise. Specifically, Table 4 compiles the biomarkers whose concentrations in normal (non-PAD) patients change significantly immediately after ("IMM") or approximately two hours ("2 HR") after the treadmill exercise. Table 5 compiles the biomarkers whose concentrations in long claudicator PAD patients change significantly immediately after or approximately two hours after the long claudicator PAD patient has endured the treadmill exercise. Table 6 compiles the biomarkers whose concentrations in PAD patients change significantly immediately after or approximately two hours after a treadmill exercise.

TABLE 1A

All patients/Pre-exercise (p values < 0.01)

| m/z | p value | array | fraction | Identity | Up/down (relative to control) |
|---|---|---|---|---|---|
| 66593.8 | 6.55E−04 | CM10 low | Fraction 4 | albumin | Up in PAD |
| 66469.3 | 7.98E−04 | CM10 high | Fraction 4 | albumin | Up in PAD |
| 41994.6 | 0.001057 | CM10 high | Fraction 4 | fetuin | Down in PAD |
| 44441.2 | 0.001876 | CM10 high | Fraction 4 | albumin (triple charged dimer) | Up in PAD |
| 99848.7 | 0.002703 | CM10 high | Fraction 4 | | Up in PAD |
| 12043.2 | 0.003087 | CM10 high | Fraction 1 | | Up in PAD |
| 11958.8 | 0.003326 | IMAC high | Fraction 4 | | Up in LC & PAD (PAD > LC) |

TABLE 1A-continued

All patients/Pre-exercise (p values < 0.01)

| m/z | p value | array | fraction | Identity | Up/down (relative to control) |
|---|---|---|---|---|---|
| 6197.9 | 0.003412 | IMAC low | Fraction 4 | | Down in LC, up in PAD |
| 10834.9 | 0.004551 | CM10 high | Fraction 4 | | Up in LC, down in PAD |
| 42056.9 | 0.006323 | CM10 low | Fraction 4 | fetuin | Down in PAD |
| 5875.5 | 0.008071 | IMAC low | Fraction 4 | | Up in PAD |
| 12180.1 | 0.008931 | IMAC high | Fraction 6 | | Up in PAD |
| 13924.3 | 0.009084 | CM10 high | Fraction 4 | transthyretin | Up in LC |
| 59116.5 | 0.009173 | CM10 high | Fraction 4 | α1B glycoprotein | Up in PAD |
| 94427.4 | 0.009607 | CM10 high | Fraction 6 | dimer of α1-antitrypsin | Up in PAD |
| 4722.6 | 0.009619 | CM10 low | Fraction 4 | | Down in PAD |
| 34271.8 | 0.009692 | CM10 high | Fraction 4 | | Up in PAD |

TABLE 1B

All patients/Pre-exercise (p values < 0.05)

| m/z | p value | array | fraction | Up/down (relative to control) |
|---|---|---|---|---|
| 13272.4 | 0.01036 | CM10 high | Fraction 4 | Down in PAD |
| 13720.2 | 0.01125 | IMAC high | Fraction 6 | Down in LC, Up in PAD |
| 3026.4 | 0.01131 | CM10 low | Fraction 1 | Down in LC, Up in PAD |
| 5028.4 | 0.01263 | IMAC low | Fraction 4 | Up in PAD |
| 74864.3 | 0.01280 | CM10 high | Fraction 4 | Up in LC, Down in PAD |
| 5487.3 | 0.01295 | IMAC low | Fraction 1 | Up in LC, Down in PAD |
| 11973.9 | 0.02319 | IMAC high | Fraction 1 | Up in PAD |
| 42279.0 | 0.02489 | IMAC high | Fraction 4 | Down in LC and PAD (LC > PAD) |
| 14695.8 | 0.02514 | IMAC low | Fraction 1 | Down in LC, Up in PAD |
| 10131.4 | 0.026474 | CM10 high | Fraction 6 | Down in LC, Up in PAD |
| 54144.9 | 0.02647 | IMAC low | Fraction 1 | Up in LC |
| 83633.2 | 0.0304 | CM10 low | Fraction 4 | Down in PAD |
| 11718.3 | 0.0304 | IMAC low | Fraction 4 | Up in LC and PAD (PAD > LC) |
| 13753.1 | 0.030664 | CM10 low | Fraction 4 | Up in LC, Down in PAD |
| 14058.2 | 0.03197 | CM10 high | Fraction 1 | Up in PAD |
| 4151.4 | 0.03309 | CM10 low | Fraction 4 | Down in LC |
| 5074.9 | 0.03309 | CM10 low | Fraction 4 | Down in PAD |
| 59195.3 | 0.03314 | CM10 low | Fraction 4 | Up in PAD |
| 94640.5 | 0.03557 | IMAC low | Fraction 4 | Down in LC |
| 6150.1 | 0.0356 | IMAC low | Fraction 1 | Up in LC and PAD |
| 14942.6 | 0.03692 | CM10 high | Fraction 1 | Up in PAD |
| 46927.5 | 0.03812 | CM10 low | Fraction 1 | Down in LC |
| 6642.9 | 0.042 | IMAC low | Fraction 6 | Up in LC, Down in PAD |
| 12315.2 | 0.04415 | IMAC high | Fraction 6 | Up in PAD |
| 8821.5 | 0.04572 | IMAC low | Fraction 6 | Down in LC and PAD (PAD > LC) |
| 4482.6 | 0.04669 | CM10 low | Fraction 4 | Down in PAD |
| 4654.9 | 0.04684 | CM10 low | Fraction 4 | Down in LC |
| 5423.7 | 0.0484 | IMAC low | Fraction 4 | Up in PAD |

TABLE 2

All Patients/immediately after exercise

| m/z | p value | array | fraction | Identity | Up/down (relative to control) |
|---|---|---|---|---|---|
| 15140.65 | 0.00707 | CM10 high | Fraction 1 | kappa chain of IgG | Down in LC, Up in PAD |
| 23651.9 | 0.00859 | CM10 high | Fraction 1 | | Up in PAD |
| 13924.3 | 0.0091 | CM10 high | Fraction 4 | transthyretin | Up in LC |
| 3026.4 | 0.01512 | CM10 low | Fraction 1 | | Up in LC |
| 13753.1 | 0.02113 | CM10 low | Fraction 4 | transthyretin | Up in LC |
| 12043.2 | 0.02273 | CM10 high | Fraction 1 | | Up in PAD |
| 5487.3 | 0.02322 | IMAC low | Fraction 1 | | Down in LC & PAD (LC > PAD) |
| 6150.1 | 0.02361 | IMAC low | Fraction 1 | | Down in LC & PAD (LC > PAD) |
| 11973.9 | 0.02453 | IMAC high | Fraction 1 | | Up in LC and PAD (PAD > LC) |
| 13959.1 | 0.02496 | IMAC high | Fraction 4 | transthyretin | Up in LC |
| 14942.6 | 0.02545 | CM10 high | Fraction 1 | | Down in LC, Up in PAD |
| 11204.5 | 0.02646 | CM10 high | Fraction 4 | | Up in LC, Down in PAD |
| 13983.7 | 0.02650 | CM10 low | Fraction 6 | | |
| 14104.0 | 0.02849 | CM10 low | Fraction 6 | | |
| 6642.9 | 0.02961 | IMAC low | Fraction 6 | | Up in LC and PAD (LC > PAD) |
| 13893.2 | 0.03106 | IMAC low | Fraction 6 | | Up in LC |
| 11958.8 | 0.03395 | IMAC high | Fraction 4 | | Up in LC and PAD (PAD > LC) |
| 3140.8 | 0.03595 | CM10 low | Fraction 1 | | Up in LC |
| 14043.1 | 0.03692 | CM10 high | Fraction 4 | | Up in LC and PAD (LC > PAD) |
| 5028.4 | 0.03833 | IMAC low | Fraction 4 | | Up in LC |
| 6635.1 | 0.04045 | IMAC low | Fraction 4 | | Up in LC |
| 44441.2 | 0.04076 | CM10 high | Fraction 4 | | Down in LC, Up in PAD |

TABLE 3

All patients/two hours after exercise

| m/z | p value | array | fraction | Up/down (relative to control) |
|---|---|---|---|---|
| 75053.2 | 0.00157 | IMAC high | Fraction 1 | Down in PAD |
| 18183.9 | 0.00773 | CM10 low | Fraction 6 | Down in LC, PAD |
| 11950.4 | 0.0078 | CM10 high | Fraction 1 | Down in LC, Up in PAD |
| 28994.6 | 0.01110 | CM10 low | Fraction 6 | |
| 17741.7 | 0.01199 | CM10 low | Fraction 6 | |
| 151061.2 | 0.01282 | IMAC high | Fraction 1 | Down in LC and PAD (LC > PAD) |
| 23530.2 | 0.01648 | CM10 low | Fraction 1 | Up in PAD |
| 17541.8 | 0.02006 | CM10 low | Fraction 6 | |
| 17374.4 | 0.02126 | CM10 high | Fraction 4 | Up in LC, Down in PAD |
| 11718.9 | 0.02184 | IMAC low | Fraction 4 | Up in LC and PAD (PAD > LC) |
| 14390.1 | 0.0244 | IMAC high | Fraction 6 | Down in LC and PAD (LC > PAD) |
| 28107.7 | 0.02551 | CM10 low | Fraction 6 | |
| 14085.8 | 0.02693 | CM10 high | Fraction 1 | Up in LC and PAD (PAD > LC) |
| 10378.1 | 0.030666 | IMAC high | Fraction 1 | Up in LC |
| 17416.5 | 0.036 | CM10 low | Fraction 6 | |
| 14483.8 | 0.03737 | IMAC high | Fraction 6 | Down in LC and PAD (LC > PAD) |
| 28140.1 | 0.04133 | IMAC high | Fraction 6 | Down in LC and PAD |
| 6642.9 | 0.04199 | IMAC low | Fraction 6 | Up in LC, Down in PAD |
| 14942.6 | 0.04415 | CM10 high | Fraction 1 | Down in LC, Up in PAD |
| 10194.1 | 0.04547 | IMAC high | Fraction 1 | Up in LC |
| 13272.4 | 0.04672 | CM10 high | Fraction 4 | Up in LC, Down in PAD |
| 15140.7 | 0.04937 | CM10 high | Fraction 1 | Down in LC, Up in PAD |
| 23651.9 | 0.04939 | CM10 high | Fraction 1 | Up in PAD |

TABLE 4

Normal patient samples (biomarker intensity changes over time)

| m/z | p value | array | fraction | Up/down (relative to pre-exercise control) |
|---|---|---|---|---|
| 22267.5 | 0.01364 | IMAC low | Fraction 4 | Up in IMM and 2 HR (2 HR > IMM) |
| 44536.2 | 0.01480 | CM10 low | Fraction 4 | Up in 2 HR |
| 66469.3 | 0.01625 | CM10 high | Fraction 4 | Up in IMM and 2 HR (2 HR > IMM) |
| 83573.1 | 0.02273 | CM10 high | Fraction 4 | Down in IMM and 2 HR (IMM > 2 HR) |
| 89098.9 | 0.0246 | CM10 low | Fraction 4 | Up in 2 HR |
| 59195.3 | 0.02564 | CM10 low | Fraction 4 | Up in 2 HR |
| 34154.2 | 0.0315 | IMAC high | Fraction 4 | Up in IMM and 2 HR (2 HR > IMM) |
| 66401.9 | 0.03524 | IMAC high | Fraction 4 | Up in IMM and 2 HR (2 HR > IMM) |
| 73315.3 | 0.04137 | CM10 low | Fraction 4 | Up in IMM and 2 HR (2 HR > IMM) |
| 3140.8 | 0.04235 | CM10 low | Fraction 1 | Up in 2 HR |
| 7933.9 | 0.04247 | CM10 low | Fraction 4 | Down in IMM and 2 HR (IMM > 2 HR) |
| 3426.7 | 0.0487 | CM10 low | Fraction 1 | Up in IMM and 2 HR |
| 5875.5 | 0.05469 | IMAC low | Fraction 4 | Up in IMM and 2 HR (2 HR > IMM) |

TABLE 5

Long claudicator patient samples (biomarker intensity changes over time)

| m/z | p value | array | fraction | Up/down (relative to pre-exercise control) |
|---|---|---|---|---|
| 10834.9 | 0.04355 | CM10 high | Fraction 4 | Down in IMM and 2 HR (IMM > 2 HR) |
| 28955.1 | 0.04355 | CM10 low | Fraction 4 | Up in IMM, Down in 2 HR |
| 3140.8 | 0.04884 | CM10 low | Fraction 1 | Up in IMM |
| 75053.2 | 0.04979 | IMAC high | Fraction 1 | Up in 2 HR |
| 5416.6 | 0.04979 | CM10 low | Fraction 4 | Up in IMM |
| 11272.6 | 0.05481 | CM10 high | Fraction 4 | Down in IMM |

TABLE 6

PAD patient samples (biomarker intensity changes over time)

| m/z | p value | array | fraction | Up/down [relative to pre-exercise control] |
|---|---|---|---|---|
| 49034.0 | 0.01731 | CM10 low | Fraction 4 | Down in IMM and 2 HR (2 HR > IMM) |
| 45240.3 | 0.02186 | CM10 low | Fraction 6 | |
| 56032.7 | 0.02872 | IMAC high | Fraction 6 | Down in IMM and 2 HR (2 HR > IMM) |
| 4654.9 | 0.04230 | CM10 low | Fraction 4 | Down in 2 HR |
| 10834.9 | 0.04352 | CM10 high | Fraction 4 | Down in IMM and 2 HR (IMM > 2 HR) |

TABLE 6-continued

PAD patient samples (biomarker intensity changes over time)

| m/z | p value | array | fraction | Up/down [relative to pre-exercise control] |
|---|---|---|---|---|
| 14811.7 | 0.04469 | IMAC high | Fraction 6 | Down in IMM and 2 HR |
| 11272.6 | 0.05481 | CM10 high | Fraction 4 | Down in IMM |

For selected biomarkers, the peak intensities measured for each subject are presented graphically in FIG. 1. As shown in FIG. 1, either the relative concentrations of the biomarkers between patient groups or the changes during the course of the described exercise regimen may be used by clinicians to qualify PAD status in test subjects.

The biomarkers of this invention were determined from mass spectra generated on a Ciphergen Biosystems, Inc., PBS II mass spectrometer. This instrument has a mass accuracy of about +/−0.15 percent. Additionally, the instrument has a mass resolution of about 400 to 1000 m/dm, where m is mass and dm is the mass spectral peak width at 0.5 peak height. The mass-to-charge ratio of the biomarkers was determined using Biomarker Wizard™ software (Ciphergen Biosystems, Inc.). Biomarker Wizard assigns a mass-to-charge ratio to a biomarker by clustering the mass-to-charge ratios of the same peaks from all the spectra analyzed, as determined by the PBSII, taking the maximum and minimum mass-to-charge-ratio in the cluster, and dividing by two. Accordingly, the masses provided reflect these specifications.

The average peak intensities measured for the biomarkers described in Tables 1-6 are shown in Tables 7-17 and described further in the Examples section. Table 18 compiles the biomarkers from various time points which were determined to be significant using the SAM test (Tusher V, et al., Proc. Natl. Acad. Sci., 98: 5116-5124 (2001).

The changes in intensity observed for particular peaks may be used to qualify PAD status in patients. For example, the approximately 66 kD albumin biomarker in fraction 4 is observed, using the CM10 array, to increase after exercise in normal patients. In contrast, in LC patients and especially in PAD patients, the increase in the intensity of this 66 kD biomarker following exercise is substantially diminished. Similarly, the intensity of the peak corresponding to the approximately 42 kD protein in fraction 4 is observed to decrease in normal and LC patients following the treadmill exercise but does not change significantly in PAD subjects. The peak intensity associated with the 13.9 kD transthyretin biomarker, on the other hand, does not change substantially as a function of exercise, but is substantially elevated in LC subjects relative to normal and PAD subjects regardless of exercise, reflecting a possible role in functional capacity for this protein.

With respect to the albumin biomarker, the data shows how the same marker can be identified under various conditions in different forms. For example, Table 18 shows that albumin is overexpressed in PAD subjects in the resting state, consistent with the view that PAD patients are in a state of chronic oxidative stress. The albumin biomarker can be observed as a 66 kD singly-charged monomer or a 44 kD triple-charged dimer on a CM10 chip read at high intensity. Similarly, overexpression of an albumin biomarker could be detected as a 22 kD or 33 kD triple or doubly-charged albumin monomer under a particular set of conditions in a sample taken from a subject at rest and similarly correlated with an increased likelihood of PAD in the subject. As described herein, one skilled in the art will recognize that the overexpression of an albumin biomarker (or any other identified biomarker) in a subject may be detected using various methods, where the methods recognize different aspects of the biomarker, e.g., biomarker epitopes (including post-translationally modified portions of the biomarker) or protein complexes comprising one or more biomarker monomers.

Because the biomarkers of this invention are characterized by mass-to-charge ratio, binding properties and spectral shape (e.g., FIG. 2), they can be detected by mass spectrometry without knowing their specific identity. However, if desired, biomarkers whose identity is not determined can be identified by, for example, determining the amino acid sequence of the polypeptides. For example, a biomarker can be peptide-mapped with a number of enzymes, such as trypsin or VS protease, and the molecular weights of the digestion fragments can be used to search databases for sequences that match the molecular weights of the digestion fragments generated by the various enzymes. Alternatively, protein biomarkers can be sequenced using tandem MS technology. In this method, the protein is isolated by, for example, gel electrophoresis. A band containing the biomarker is cut out and the protein is subject to protease digestion. Individual protein fragments are separated by a first mass spectrometer. The fragment is then subjected to collision-induced cooling, which fragments the peptide and produces a polypeptide ladder. A polypeptide ladder is then analyzed by the second mass spectrometer of the tandem MS. The difference in masses of the members of the polypeptide ladder identifies the amino acids in the sequence. An entire protein can be sequenced this way, or a sequence fragment can be subjected to database mining to find identity candidates.

The preferred biological source for detection of the biomarkers is blood plasma. However, in other embodiments, the biomarkers can be detected in other body fluids and tissues, e.g., blood serum, cerebrospinal fluid, urine, semen, etc.

The biomarkers of this invention are biomolecules. Accordingly, this invention provides these biomolecules in isolated form. The biomarkers can be isolated from biological fluids, such as blood plasma, serum or cerebrospinal fluid. They can be isolated by any method known in the art, based on both their mass and their binding characteristics. For example, a sample comprising the biomolecules can be subject to chromatographic fractionation, as described herein, and subject to further separation by, e.g., acrylamide gel electrophoresis. Knowledge of the identity of the biomarkers also allows their isolation by immunoaffinity chromatography.

III. Detection of Biomarkers for Qualifying PAD Status

The biomarkers of this invention can be detected by any suitable method. Detection paradigms that can be employed to this end include optical methods, electrochemical methods (voltametry and amperometry techniques), atomic force microscopy, and radio frequency methods, e.g., multipolar resonance spectroscopy. Illustrative of optical methods, in addition to microscopy, both confocal and non-confocal, are detection of fluorescence, luminescence, chemiluminescence, absorbance, reflectance, transmittance, and birefringence or refractive index (e.g., surface plasmon resonance, ellipsometry, a resonant mirror method, a grating coupler waveguide method or interferometry).

In one embodiment, a sample is analyzed by means of a biochip. Biochips generally comprise solid substrates and have a generally planar surface, to which a capture reagent (also called an adsorbent or affinity reagent) is attached. Frequently, the surface of a biochip comprises a plurality of addressable locations, each of which has the capture reagent bound there.

"Protein biochip" refers to a biochip adapted for the capture of polypeptides. Many protein biochips are described in the art. These include, for example, protein biochips produced by Ciphergen Biosystems, Inc. (Fremont, Calif.), Packard BioScience Company (Meriden Conn.), Zyomyx (Hayward, Calif.), Phylos (Lexington, Mass.) and Biacore (Uppsala, Sweden). Examples of such protein biochips are described in the following patents or published patent applications: U.S. Pat. No. 6,225,047; PCT International Publication No. WO 99/51773; U.S. Pat. No. 6,329,209, PCT International Publication No. WO 00/56934 and U.S. Pat. No. 5,242,828.

A. Detection by Mass Spectrometry

In a preferred embodiment, the biomarkers of this invention are detected by mass spectrometry, a method that employs a mass spectrometer to detect gas phase ions. Examples of mass spectrometers are time-of-flight, magnetic sector, quadrupole filter, ion trap, ion cyclotron resonance, electrostatic sector analyzer and hybrids of these.

In a further preferred method, the mass spectrometer is a laser desorption/ionization mass spectrometer. In laser desorption/ionization mass spectrometry, the analytes are placed on the surface of a mass spectrometry probe, a device adapted to engage a probe interface of the mass spectrometer and to present an analyte to ionizing energy for ionization and introduction into a mass spectrometer. A laser desorption mass spectrometer employs laser energy, typically from an ultraviolet laser, but also from an infrared laser, to desorb analytes from a surface, to volatilize and ionize them and make them available to the ion optics of the mass spectrometer.

1. SELDI

A preferred mass spectrometric technique for use in the invention is "Surface Enhanced Laser Desorption and Ionization" or "SELDI," as described, for example, in U.S. Pat. No. 5,719,060 and No. 6,225,047, both to Hutchens and Yip. This refers to a method of desorption/ionization gas phase ion spectrometry (e.g., mass spectrometry) in which an analyte (here, one or more of the biomarkers) is captured on the surface of a SELDI mass spectrometry probe. There are several versions of SELDI.

One version of SELDI is called "affinity capture mass spectrometry." It also is called "Surface-Enhanced Affinity Capture" or "SEAC". This version involves the use of probes that have a material on the probe surface that captures analytes through a non-covalent affinity interaction (adsorption) between the material and the analyte. The material is variously called an "adsorbent," a "capture reagent," an "affinity reagent" or a "binding moiety." Such probes can be referred to as "affinity capture probes" and as having an "adsorbent surface." The capture reagent can be any material capable of binding an analyte. The capture reagent may be attached directly to the substrate of the selective surface, or the substrate may have a reactive surface that carries a reactive moiety that is capable of binding the capture reagent, e.g., through a reaction forming a covalent or coordinate covalent bond. Epoxide and carbodiimidizole are useful reactive moieties to covalently bind polypeptide capture reagents such as antibodies or cellular receptors. Nitriloacetic acid and iminodiacetic acid are useful reactive moieties that function as chelating agents to bind metal ions that interact non-covalently with histidine containing peptides. Adsorbents are generally classified as chromatographic adsorbents and biospecific adsorbents.

"Chromatographic adsorbent" refers to an adsorbent material typically used in chromatography. Chromatographic adsorbents include, for example, ion exchange materials, metal chelators (e.g., nitriloacetic acid or iminodiacetic acid), immobilized metal chelates, hydrophobic interaction adsorbents, hydrophilic interaction adsorbents, dyes, simple biomolecules (e.g., nucleotides, amino acids, simple sugars and fatty acids) and mixed mode adsorbents (e.g., hydrophobic attraction/electrostatic repulsion adsorbents).

"Biospecific adsorbent" refers to an adsorbent comprising a biomolecule, e.g., a nucleic acid molecule (e.g., an aptamer), a polypeptide, a polysaccharide, a lipid, a steroid or a conjugate of these (e.g., a glycoprotein, a lipoprotein, a glycolipid, a nucleic acid (e.g., DNA)-protein conjugate). In certain instances, the biospecific adsorbent can be a macromolecular structure such as a multiprotein complex, a biological membrane or a virus. Examples of biospecific adsorbents are antibodies, receptor proteins and nucleic acids. Biospecific adsorbents typically have higher specificity for a target analyte than chromatographic adsorbents. Further examples of adsorbents for use in SELDI can be found in U.S. Pat. No. 6,225,047. A "bioselective adsorbent" refers to an adsorbent that binds to an analyte with an affinity of at least $10^{-8}$ M.

Protein biochips produced by Ciphergen Biosystems, Inc. comprise surfaces having chromatographic or biospecific adsorbents attached thereto at addressable locations. Ciphergen ProteinChip® arrays include NP20 (hydrophilic); H4 and HSO (hydrophobic); SAX-2, Q-10 and LSAX-30 (anion exchange); WCX-2, CM-10 and LWCX-30 (cation exchange); IMAC-3, IMAC-30 and IMAC 40 (metal chelate); and PS-10, PS-20 (reactive surface with carboimidizole, expoxide) and PG-20 (protein G coupled through carboimidizole). Hydrophobic ProteinChip arrays have isopropyl or nonylphenoxy-poly(ethylene glycol)methacrylate functionalities. Anion exchange ProteinChip arrays have quaternary ammonium functionalities. Cation exchange ProteinChip arrays have carboxylate functionalities. Immobilized metal chelate ProteinChip arrays have nitriloacetic acid functionalities that adsorb transition metal ions, such as copper, nickel, zinc, and gallium, by chelation. Preactivated ProteinChip arrays have carboimidizole or epoxide functional groups that can react with groups on proteins for covalent binding.

Such biochips are further described in: U.S. Pat. No. 6,579,719 (Hutchens and Yip, "Retentate Chromatography," Jun. 17, 2003); PCT International Publication No. WO 00/66265 (Rich et al., "Probes for a Gas Phase Ion Spectrometer," Nov. 9, 2000); U.S. Pat. No. 6,555,813 (Beecher et al., "Sample Holder with Hydrophobic Coating for Gas Phase Mass Spectrometer," Apr. 29, 2003); U.S. Patent Application No. U.S. 2003 0032043 A1 (Pohl and Papanu, "Latex Based Adsorbent Chip," Jul. 16, 2002); and PCT International Publication No. WO 03/040700 (Um et al., "Hydrophobic Surface Chip," May 15, 2003); U.S. Provisional Patent Application No. 60/367,837 (Boschetti et al., "Biochips With Surfaces Coated With Polysaccharide-Based Hydrogels," May 5, 2002) and the U.S. patent application entitled "Photocrosslinked Hydrogel Surface Coatings" (Huang et al., filed Feb. 21, 2003).

In general, a probe with an adsorbent surface is contacted with the sample for a period of time sufficient to allow biomarker or biomarkers that may be present in the sample to bind to the adsorbent. After an incubation period, the substrate is washed to remove unbound material. Any suitable washing solutions can be used; preferably, aqueous solutions are employed. The extent to which molecules remain bound can be manipulated by adjusting the stringency of the wash. The elution characteristics of a wash solution can depend, for example, on pH, ionic strength, hydrophobicity, degree of chaotropism, detergent strength, and temperature. Unless the probe has both SEAC and SEND properties (as described herein), an energy absorbing molecule then is applied to the substrate with the bound biomarkers.

The biomarkers bound to the substrates are detected in a gas phase ion spectrometer such as a time-of-flight mass spectrometer. The biomarkers are ionized by an ionization source such as a laser, the generated ions are collected by an ion optic assembly, and then a mass analyzer disperses and analyzes the passing ions. The detector then translates information of the detected ions into mass-to-charge ratios. Detection of a biomarker typically will involve detection of signal intensity. Thus, both the quantity and mass of the biomarker can be determined.

Another version of SELDI is Surface-Enhanced Neat Desorption (SEND), which involves the use of probes comprising energy absorbing molecules that are chemically bound to the probe surface ("SEND probe"). The phrase "energy absorbing molecules" (EAM) denotes molecules that are capable of absorbing energy from a laser desorption/ionization source and, thereafter, contribute to desorption and ionization of analyte molecules in contact therewith. The EAM category includes molecules used in MALDI, frequently referred to as "matrix," and is exemplified by cinnamic acid derivatives, sinapinic acid (SPA), cyano-hydroxy-cinnamic acid (CHCA) and dihydroxybenzoic acid, ferulic acid, and hydroxyacetophenone derivatives. In certain embodiments, the energy absorbing molecule is incorporated into a linear or cross-linked polymer, e.g., a polymethacrylate. For example, the composition can be a co-polymer of a-cyano-4-methacryloyloxycinnamic acid and acrylate. In another embodiment, the composition is a co-polymer of a-cyano-4-methacryloyloxycinnamic acid, acrylate and 3-(tri-ethoxy)silyl propyl methacrylate. In another embodiment, the composition is a co-polymer of a-cyano-4-methacryloyloxycinnamic acid and octadecylmethacrylate ("C18 SEND"). SEND is further described in U.S. Pat. No. 6,124,137 and PCT International Publication No. WO 03/64594 (Kitagawa, "Monomers And Polymers Having Energy Absorbing Moieties Of Use In Desorption/Ionization Of Analytes," Aug. 7, 2003).

SEAC/SEND is a version of SELDI in which both a capture reagent and an energy absorbing molecule are attached to the sample presenting surface. SEAC/SEND probes therefore allow the capture of analytes through affinity capture and ionization/desorption without the need to apply external matrix. The C18 SEND biochip is a version of SEAC/SEND, comprising a C18 moiety which functions as a capture reagent, and a CHCA moiety which functions as an energy absorbing moiety.

Another version of SELDI, called Surface-Enhanced Photolabile Attachment and Release (SEPAR), involves the use of probes having moieties attached to the surface that can covalently bind an analyte, and then release the analyte through breaking a photolabile bond in the moiety after exposure to light, e.g., to laser light (see, U.S. Pat. No. 5,719,060). SEPAR and other forms of SELDI are readily adapted to detecting a biomarker or biomarker profile, pursuant to the present invention.

2. Other Mass Spectrometry Methods

In another mass spectrometry method, the biomarkers can be first captured on a chromatographic resin having chromatographic properties that bind the biomarkers. In the present example, this could include a variety of methods. For example, one could capture the biomarkers on a cation exchange resin, such as CM Ceramic HyperD F resin, wash the resin, elute the biomarkers and detect by MALDI. Alternatively, this method could be preceded by fractionating the sample on an anion exchange resin before application to the cation exchange resin. In another alternative, one could fractionate on an anion exchange resin and detect by MALDI directly. In yet another method, one could capture the biomarkers on an immuno-chromatographic resin that comprises antibodies that bind the biomarkers, wash the resin to remove unbound material, elute the biomarkers from the resin and detect the eluted biomarkers by MALDI or by SELDI.

3. Data Analysis

Analysis of analytes by time-of-flight mass spectrometry generates a time-of-flight spectrum. The time-of-flight spectrum ultimately analyzed typically does not represent the signal from a single pulse of ionizing energy against a sample, but rather the sum of signals from a number of pulses. This reduces noise and increases dynamic range. This time-of-flight data is then subject to data processing. In Ciphergen's ProteinChip® software, data processing typically includes TOF-to-M/Z transformation to generate a mass spectrum, baseline subtraction to eliminate instrument offsets and high frequency noise filtering to reduce high frequency noise.

Data generated by desorption and detection of biomarkers can be analyzed with the use of a programmable digital computer. The computer program analyzes the data to indicate the number of biomarkers detected, and optionally the strength of the signal and the determined molecular mass for each biomarker detected. Data analysis can include steps of determining signal strength of a biomarker and removing data deviating from a predetermined statistical distribution. For example, the observed peaks can be normalized, by calculating the height of each peak relative to some reference. The reference can be background noise generated by the instrument and chemicals such as the energy absorbing molecule which is set at zero in the scale.

The computer can transform the resulting data into various formats for display. The standard spectrum can be displayed, but in one useful format only the peak height and mass information are retained from the spectrum view, yielding a cleaner image and enabling biomarkers with nearly identical molecular weights to be more easily seen. In another useful format, two or more spectra are compared, conveniently highlighting unique biomarkers and biomarkers that are up- or down-regulated between samples. Using any of these formats, one can readily determine whether a particular biomarker is present in a sample.

Analysis generally involves the identification of peaks in the spectrum that represent signal from an analyte. Peak selection can be done visually, but software is available, as part of Ciphergen's ProteinChip® software package, that can automate the detection of peaks. In general, this software functions by identifying signals having a signal-to-noise ratio above a selected threshold and labeling the mass of the peak at the centroid of the peak signal. In one useful application, many spectra are compared to identify identical peaks present in some selected percentage of the mass spectra. One version of this software clusters all peaks appearing in the various spectra within a defined mass range, and assigns a mass (M/Z) to all the peaks that are near the mid-point of the mass (M/Z) cluster.

Software used to analyze the data can include code that applies an algorithm to the analysis of the signal to determine whether the signal represents a peak in a signal that corresponds to a biomarker according to the present invention. The software also can subject the data regarding observed biomarker peaks to classification tree or ANN analysis, to determine whether a biomarker peak or combination of biomarker peaks is present that indicates the status of the particular clinical parameter under examination.

Figure 2:
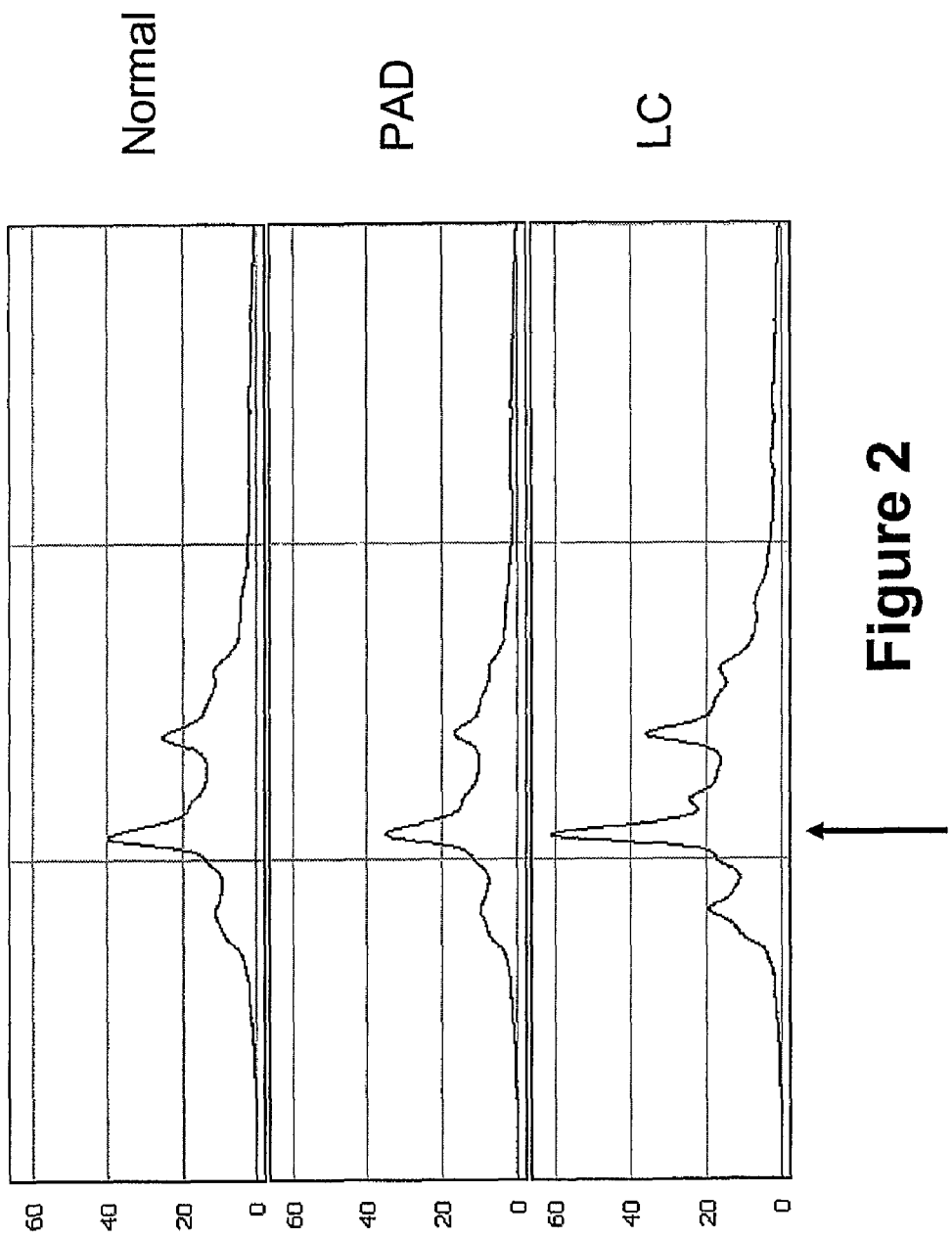
FIG. 2 shows representative SELDI-TOF spectra for the PAD biomarker transthyretin observed in samples taken from normal, LC and PAD subjects (top to bottom). The y-axis corresponds to the measured intensity of the peaks and the x axis corresponds to m/z values. The peaks shown were observed in Fraction 4 following Hyper Q DF fractionation, on a CM10 array read at high laser intensity, as shown in FIG. 1U. Arrows indicate the position of the peak corresponding to the 13.9 kDa transthyretin biomarker.

Analysis of the data may be "keyed" to a variety of parameters that are obtained, either directly or indirectly, from the mass spectrometric analysis of the sample. These parameters include, but are not limited to, the presence or absence of one or more peaks, the shape of a peak or group of peaks, the height of one or more peaks, the log of the height of one or more peaks, and other arithmetic manipulations of peak height data. The shape of a representative biomarker peak is shown in FIG. 2.

B. Detection by Immunoassay

In another embodiment, the biomarkers of this invention can be measured by immunoassay. Immunoassay requires biospecific capture reagents, such as antibodies, to capture the biomarkers. Antibodies can be produced by methods well known in the art, e.g., by immunizing animals with the biomarkers. Biomarkers can be isolated from samples based on their binding characteristics. Alternatively, if the amino acid sequence of a polypeptide biomarker is known, the polypeptide can be synthesized and used to generate antibodies by methods well known in the art.

This invention contemplates traditional immunoassays including, for example, sandwich immunoassays including ELISA or fluorescence-based immunoassays, as well as other enzyme immunoassays. In the SELDI-based immunoassay, a biospecific capture reagent for the biomarker is attached to the surface of an MS probe, such as a pre-activated Protein-Chip array. The biomarker is then specifically captured on the biochip through this reagent, and the captured biomarker is detected by mass spectrometry.

For the purposes of qualifying PAD status in a patient, the biomarkers identified herein as useful include, in addition to the specific peaks listed in the Tables, amino acid variants and post-translationally modified forms of the corresponding proteins.

IV. Determination of Subject PAD Status

A. Single Markers

The biomarkers of the invention can be used in diagnostic tests to assess PAD status in a subject, e.g., to diagnose PAD. The phrase "PAD status" includes distinguishing, inter alia, PAD v. normal (non-PAD) and, in particular, PAD v normal, or PAD v. long claudicator PAD (LC PAD). Based on this status, further procedures may be indicated, including additional diagnostic tests or therapeutic procedures or regimens.

The power of a diagnostic test to correctly predict status is commonly measured as the sensitivity of the assay, the specificity of the assay or the area under a receiver operated characteristic ("ROC") curve. Sensitivity is the percentage of true positives that are predicted by a test to be positive, while specificity is the percentage of true negatives that are predicted by a test to be negative. An ROC curve provides the sensitivity of a test as a function of 1-specificity. The greater the area under the ROC curve, the more powerful the predictive value of the test. Other useful measures of the utility of a test are positive predictive value and negative predictive value. Positive predictive value is the percentage of actual positives who test as positive. Negative predictive value is the percentage of actual negatives that test as negative.

The biomarkers of this invention show a statistical difference in different PAD statuses of at least $p \leq 0.05$, $p \leq 10^{-2}$, $p \leq 10^{-3}$, $p \leq 10^{-4}$ or $p \leq 10^{-5}$. Diagnostic tests that use these biomarkers alone or in combination show a sensitivity and specificity of at least 75%, at least 80%, at least 85%, at least 90%, at least 95%, at least 98% and about 100%.

Each biomarker listed in Table 1, for example, is differentially present in normal subjects, PAD subjects, or LC PAD subjects; therefore, each biomarker is individually useful in aiding in the determination of PAD status. The method involves, first, measuring the selected biomarker in a subject sample using the methods described herein, e.g., capture on a SELDI biochip followed by detection by mass spectrometry and, second, comparing the measurement with a diagnostic amount or cut-off that distinguishes a positive PAD status from a negative PAD status (e.g., a "normal" patient). The diagnostic amount represents a measured amount of a biomarker above which or below which a subject is classified as having a particular PAD status (e.g., an LC PAD patient versus a normal patient or a PAD patient exhibiting typical claudication times). For example, if the biomarker is up-regulated compared to normal during PAD, then a measured amount above the diagnostic cut-off provides a diagnosis of PAD. Alternatively, if the biomarker is down-regulated during PAD, then a measured amount below the diagnostic cut-off provides a diagnosis of PAD. As is well understood in the art, by adjusting the particular diagnostic cut-off used in an assay, one can increase sensitivity or specificity of the diagnostic assay depending on the preference of the diagnostician. The particular diagnostic cut-off can be determined, for example, by measuring the amount of the biomarker in a statistically significant number of samples from subjects with the different PAD statuses, as was done here, and drawing the cut-off to suit the diagnostician's desired levels of specificity and sensitivity.

B. Combinations of Markers

While individual biomarkers are useful diagnostic biomarkers, it has been found that a combination of biomarkers can provide greater predictive value of a particular status than single biomarkers alone. Specifically, the detection of a plurality of biomarkers in a sample can increase the sensitivity and/or specificity of the test.

The protocols described herein may be used to generate mass spectra from patient samples. The peak masses and heights are then abstracted into a discovery data set. This data set is used to train a learning algorithm employing classification and regression tree analysis (CART) (Ciphergen Biomarker Patterns Software™). In particular, CART chooses many subsets of the peaks at random. For each subset, CART generates a best or near best decision tree to classify a sample as, e.g., PAD or non-PAD.

C. Subject Management

In certain embodiments of the methods of qualifying PAD status, the methods further comprise managing subject treatment based on the status. Such management includes the actions of the physician or clinician subsequent to determining PAD status. For example, if a physician makes a diagnosis of PAD, then a certain regime of treatment may be prescribed. A suitable regime of treatment may include, without limitation, a supervised exercise program; control of blood pressure, sugar intake, and/or lipid levels; cessation of smoking, including any necessary counseling and nicotine replacement; and drug therapies including the administration of aspirin (with or without dipyridamole), clopidogrel, cilostazol, and/or pentoxifylline. Alternatively, a diagnosis of PAD might be followed by further testing to determine whether a patient is suffering from a specific form of PAD, or whether the patient is suffering from related diseases such as coronary artery disease. Also, if the diagnostic test gives an inconclusive result on PAD status, further tests may be called for.

V. Generation of Classification Algorithms for Qualifying PAD Status

In some embodiments, data derived from the spectra (e.g., mass spectra or time-of-flight spectra) that are generated using samples such as "known samples" can then be used to "train" a classification model. A "known sample" is a sample that has been pre-classified. The data that are derived from the spectra and are used to form the classification model can be referred to as a "training data set." Once trained, the classification model can recognize patterns in data derived from spectra generated using unknown samples. The classification model can then be used to classify the unknown samples into classes. This can be useful, for example, in predicting whether or not a particular biological sample is associated with a certain biological condition (e.g., diseased versus non-diseased).

The training data set that is used to form the classification model may comprise raw data or pre-processed data. In some embodiments, raw data can be obtained directly from time-of-flight spectra or mass spectra, and then may be optionally "pre-processed" as described above.

Classification models can be formed using any suitable statistical classification (or "learning") method that attempts to segregate bodies of data into classes based on objective parameters present in the data. Classification methods may be either supervised or unsupervised. Examples of supervised and unsupervised classification processes are described in Jain, "Statistical Pattern Recognition: A Review", *IEEE Transactions on Pattern Analysis and Machine Intelligence*, Vol. 22, No. 1, January 2000, the teachings of which are incorporated by reference.

In supervised classification, training data containing examples of known categories are presented to a learning mechanism, which learns one or more sets of relationships that define each of the known classes. New data may then be applied to the learning mechanism, which then classifies the new data using the learned relationships. Examples of supervised classification processes include linear regression processes (e.g., multiple linear regression (MLR), partial least squares (PLS) regression and principal components regression (PCR)), binary decision trees (e.g., recursive partitioning processes such as CART—classification and regression trees), artificial neural networks such as back propagation networks, discriminant analyses (e.g., Bayesian classifier or Fischer analysis), logistic classifiers, and support vector classifiers (support vector machines).

A preferred supervised classification method is a recursive partitioning process. Recursive partitioning processes use recursive partitioning trees to classify spectra derived from unknown samples. Further details about recursive partitioning processes are provided in U.S. Patent Application No. 2002 0138208 A1 to Paulse et al., "Method for analyzing mass spectra."

In other embodiments, the classification models that are created can be formed using unsupervised learning methods. Unsupervised classification attempts to learn classifications based on similarities in the training data set, without pre-classifying the spectra from which the training data set was derived. Unsupervised learning methods include cluster analyses. A cluster analysis attempts to divide the data into "clusters" or groups that ideally should have members that are very similar to each other, and very dissimilar to members of other clusters. Similarity is then measured using some distance metric, which measures the distance between data items, and clusters together data items that are closer to each other. Clustering techniques include the MacQueen's K-means algorithm and the Kohonen's Self-Organizing Map algorithm.

Learning algorithms asserted for use in classifying biological information are described, for example, in PCT International Publication No. WO 01/31580 (Barnhill et al., Methods and devices for identifying patterns in biological systems and methods of use thereof), U.S. Patent Application No. 2002 0193950 A1 (Gavin et al., "Method or analyzing mass spectra"), U.S. Patent Application No. 2003 0004402 A1 (Hitt et al., "Process for discriminating between biological states based on hidden patterns from biological data"), and U.S. Patent Application No. 2003 0055615 A1 (Zhang and Zhang, "Systems and methods for processing biological expression data").

The classification models can be formed on and used on any suitable digital computer. Suitable digital computers include micro, mini, or large computers using any standard or specialized operating system, such as a Unix, Windows™ or Linux™ based operating system. The digital computer that is used may be physically separate from the mass spectrometer that is used to create the spectra of interest, or it may be coupled to the mass spectrometer.

The training data set and the classification models according to embodiments of the invention can be embodied by computer code that is executed or used by a digital computer. The computer code can be stored on any suitable computer readable media including optical or magnetic disks, sticks, tapes, etc., and can be written in any suitable computer programming language including C, C++, visual basic, etc.

The learning algorithms described above are useful both for developing classification algorithms for the biomarkers already discovered, or for finding new biomarkers for PAD. The classification algorithms, in turn, form the base for diagnostic tests by providing diagnostic values (e.g., cut-off points) for biomarkers used singly or in combination.

VI. Kits for Detection of Biomarkers for Peripheral Artery Disease

In another aspect, the present invention provides kits for qualifying Peripheral artery disease status, which kits are used to detect biomarkers according to the invention. In one embodiment, the kit comprises a solid support, such as a chip, a microliter plate or a bead or resin having a capture reagent attached thereon, wherein the capture reagent binds a biomarker of the invention. Thus, for example, the kits of the present invention can comprise mass spectrometry probes for SELDI, such as ProteinChip® arrays. In the case of bio-specfic capture reagents, the kit can comprise a solid support with a reactive surface, and a container comprising the bio-specific capture reagent.

The kit can also comprise a washing solution or instructions for making a washing solution, in which the combination of the capture reagent and the washing solution allows capture of the biomarker or biomarkers on the solid support for subsequent detection by, e.g., mass spectrometry. The kit may include more than type of adsorbent, each present on a different solid support.

In a further embodiment, such a kit can comprise instructions for suitable operational parameters in the form of a label or separate insert. For example, the instructions may inform a consumer about how to collect the sample, how to wash the probe or the particular biomarkers to be detected.

In yet another embodiment, the kit can comprise one or more containers with biomarker samples, to be used as standard(s) for calibration.

VII. Use of Biomarkers for PAD in Screening Assays

The methods of the present invention have other applications as well. For example, the biomarkers can be used to screen for compounds that modulate the expression of the biomarkers in vitro or in vivo, which compounds in turn may be useful in treating or preventing PAD in patients. In another example, the biomarkers can be used to monitor the response to treatments for PAD. In yet another example, the biomarkers can be used in heredity studies to determine if the subject is at risk for developing PAD.

Thus, for example, the kits of this invention could include a solid substrate having a hydrophilic, metal chelate, or cation exchange function, such as a protein biochip (e.g., a Ciphergen NP20, IMAC30, or CM10 ProteinChip array, respectively) and a buffer for washing the substrate, as well as instructions providing a protocol to measure the biomarkers of this invention on the chip and to use these measurements to diagnose PAD.

The invention will be described in greater detail by way of specific examples. The following examples are offered for illustrative purposes, and are not intended to limit the invention in any manner. Those of skill in the art will readily recognize a variety of non-critical parameters that can be changed or modified to yield essentially the same results.

VIII. Example 1

The biomarkers were discovered using SELDI technology employing ProteinChip arrays from Ciphergen Biosystems, Inc. (Fremont, Calif.) ("Ciphergen"). The study set consisted of 20 patients with PAD and 11 age-matched controls. Subjects placed in the PAD group were those with an ankle-brachial index of 0.9 or less. All subjects underwent a treadmill test according to the Skinner-Gardner protocol (Gardner A W et al., *Med Sci Sports Exerc.*, 24:163-170 (1992)). Briefly, subjects were asked to walk on a flat treadmill operating at 2 miles per hour. The speed of the treadmill was increased 2% every two minutes. Subjects were instructed to indicate when leg claudication began and then to walk as long as they could endure the pain. Four of the 20 patients with PAD were defined to be long claudicators ("LC") due to an absolute claudication time of greater than 12 minutes, i.e., LC subjects were able to endure for longer periods the pain induced by walking relative to other members of the PAD group.

For each participant in each group, three plasma samples were analyzed for each participant: a baseline sample (before exercise), a sample taken immediately after an exercise treadmill test, and a third sample taken 2 hours after the exercise treadmill test. Therefore, 93 plasma samples were analyzed in total. Each plasma sample was subjected to fractionation on a QhyperDF column before analysis using Ciphergen's ProteinChips, as described in the detailed protocol below. After fractionation, selected fractions were analyzed using Ciphergen's IMAC30 or CM10 ProteinChips. The spectra of polypeptides in the samples were generated by time-of-flight mass spectrometry on a Ciphergen PBSE mass spectrometer. The spectra thus obtained were analyzed by Ciphergen Express™ Data Manager Software with Biomarker Wizard and Biomarker Pattern Software from Ciphergen Biosystems, Inc.

Fractions 1, 4, and 6 from the Qhyper DF fractionation were profiled using Ciphergen's IMAC30 and CM10 arrays, using the following materials and methods.

A. Q Hyper DF Anion Exchange Fractionation
Buffer List for anion exchange fractionation:
U1 (1M urea, 0.22% CHAPS, 50 mM Tris-HCl pH9)
50 mM Tris-HCl with 0.1% OGP pH9 (Wash buffer 1)
50 mM Hepes with 0.1% OGP pH7 (Wash buffer 2)
100 mM NaAcetate with 0.1% OGP pH5 (Wash buffer 3)
100 mM NaAcetate with 0.1% OGP pH4 (Wash buffer 4)
33.3% isopropanol/16.7% acetonitrile/0.1% trifluoracetic acid (Wash buffer 5)

Note: do not aliquot wash buffer 5 into the buffer tray until wash buffer 4 is being applied to the resin. This ensures that evaporation of the volatile organic solvents will not be an issue.

Material List:
Filter plate
5 v-well 96 well dishes, labeled F1-F5.
 a. Wash Resin
Prepare resin by washing Hyper Q DF resin (BioSepra, Cergy, France) 3 times with 5 bed volumes 50 mM Tris-HCl pH9. Then store in 50 mM Tris-HCl pH9 in a 50% suspension.
 b. Equilibrate Resin
Add 125 µL Hyper Q DF to each well in filter plate
Filter buffer
Add 150 µL U1 to each well
Filter buffer
Add 150 µL U1 to each well
Filter buffer
Add 150 µL U1 to each well
Filter buffer
 c. Bind Blood Plasma with Resin
Pipet 150 µL of sample from each tube to appropriate well in filter plate Vortex 30' at 4°
 d. Collect Fractions
Place v-well 96 well plate F1 under filter plate
Collect flow-through in plate F1
Add 100 µL of wash buffer 1 to each well of filter plate
Vortex 10' at Room Temperature (RT)
Collect pH 9 eluant in plate F1
Fraction 1 contains the flow through and the pH 9 eluant.
Add 100 µL of wash buffer 2 to each well of filter plate
Vortex 10' at Room Temperature (RT)
Place v-well 96 well plate F2 under filter plate
Collect fraction 2 in plate F2
Add 100 µL of wash buffer 2 to each well of filter plate
Vortex 10' at Room Temperature (RT)
Collect remainder of fraction 2 in plate F2
Fraction 2 contains the pH 7 eluant.
Add 100 µL of wash buffer 3 to each well of filter plate
Vortex 10' at Room Temperature (RT)
Place v-well 96 well plate F3 under filter plate
Collect fraction 3 in plate F3
Add 100 µL of wash buffer 3 to each well of filter plate
Vortex 10' at Room Temperature (RT)
Collect remainder of fraction 3 in plate F3
Fraction 3 contains the pH 5 eluant.
Add 100 µL of wash buffer 4 to each well of filter plate
Vortex 10' at Room Temperature (RT)
Place v-well 96 well plate F4 under filter plate
Collect fraction 4 in plate F4
Add 100 µL of wash buffer 4 to each well of filter plate Vortex 10' at Room Temperature (RT)
Collect remainder of fraction 4 in plate F4
Fraction 4 contains the pH 4 eluant.
Add 100 μL of wash buffer 5 to each well of filter plate
Vortex 10' at Room Temperature (RT)
Place v-well 96 well plate F5 under filter plate
Collect fraction 5 in plate F5
Add 100 μL of wash buffer 5 to each well of filter plate
Vortex 10' at Room Temperature (RT)
Collect remainder of fraction 5 in plate F5
Fraction 5 contains the organic solvent eluant.
Freeze until proceeding with chip binding protocol B. Chip Binding Protocol Chip Washing Buffer List:

IMAC30 array (Ciphergen Biosystems, Inc.): a suitable wash includes, but is not limited to, 50 mM Tris pH 8.0 supplemented with 500 mM NaCl.

NP20 array (Ciphergen Biosystems, Inc.): a suitable wash includes, but is not limited to, 5 mM Hepes pH 7.0 and deionized water.

CM10 array (Ciphergen Biosystems, Inc.): a suitable wash includes, but is not limited to, 100 mM ammonium acetate pH 4.0

Array Preparation:
Place arrays into bioprocessor
Load IMAC30 arrays with copper
Load 50 μl of $CuSO_4$ onto each spot of the IMAC30 array
Vortex 15' at Room Temperature (RT)
Remove $CuSO_4$ and repeat.
Water rinse
Equilibrate Arrays:
Add 100 μl chip washing buffer appropriate to the array to each well
Vortex 5' at RT
Remove buffer after vortex
Add 100 μl chip washing buffer appropriate to the array to each well
Vortex 5' at RTk
Remove buffer after vortex
Bind Plasma Fractions from Hyper Q DF, C4 or Immunoaffinity Columns to Arrays:
Add 60 μl chip washing buffer appropriate to the array to each well
Add 20 μl plasma fraction
Vortex 30' at RT
Remove sample and buffer
Wash arrays:
Add 100 μl chip washing buffer appropriate to the array to each well
Vortex 5' at RT
Remove buffer after vortex
Add 100 μl chip washing buffer appropriate to the array to each well
Vortex 5' at RT
Remove buffer after vortex
Add 100 μl chip washing buffer appropriate to the array to each well
Vortex 5' at RT Remove buffer after vortex
Water rinse 2 times
Add Matrix:
Remove Bioprocessor top and gasket
Allow the arrays to dry
SPA:
Add 0.8 μl 50% SPA (sinapinic acid) in 50% Acetonitrile and 0.5% TFA
Air dry
Add 0.8 μl 50% SPA
Air dry
CHCA
Add 0.8 μl 20% CHCA dissolved in 50% Acetonitrile+ 0.5%
Air dry
Add 0.8 μl 20% CHCA
Air dry C. Data Acquisition Settings Energy absorbing molecule: 50% SPA
Set high mass to 100000 Daltons, optimized from 2000 Daltons to 100000 Daltons.
Set starting laser intensity to 200.
Set starting detector sensitivity to 8.
Focus mass at 8000 Daltons.
Set Mass Deflector to 1000 Daltons.
Set data acquisition method to Seldi Quantitation
Set Seldi acquisition parameters 20. delta to 4. transients per to 10 ending position to 80.
Set warming positions with 2 shots at intensity 225 (don't include warming shots).
Process sample.

D. Measurement and Analysis of Biomarker Peak Intensities

Univariate analysis was performed using the Kruskal-Wallis test to compare peak intensities at a particular time point across all three groups: (1) control or "normal" subjects; (2) subjects with PAD, and (3) subjects with PAD who are also long claudicators ("long claudicator PAD"). The Kruskal-Wallis test was used to compare all three patient groups at a given time point (e.g., baseline (before exercise), immediately after exercise, or 2 hours after exercise, as defined above). For example, a p value of 0.05 or lower obtained with the Kruskal-Wallis test for a particular biomarker indicates that, at a given time point (e.g., before exercise), on a given chip (e.g., an IMAC30 chip), the biomarker may be found in a particular fraction (e.g., fraction 4 of on a QHyper DF column) at significantly higher or lower concentration in one patient group relative to another.

The Kruskal-Wallis test was also used to analyze peak differences over time within each patient group. In this analysis, a p value of 0.05 or lower obtained with the Kruskal-Wallis test for a particular biomarker indicates that, for a particular patient status (e.g., a subject with PAD), on a given chip (e.g., an IMAC30 chip), the biomarker may be found in a particular fraction (e.g., fraction 4 of on a QHyper DF column) at a significantly higher or lower concentration at one point time point relative to another (e.g., the intensity of a peak associated with the biomarker may increase significantly 2 hours after exercise relative to pre-exercise).

The Mann-Whitney test was also used to directly compare peaks observed in two groups at a particular time point, or when directly comparing peaks observed at two time points within a particular group.

Finally, the Significance Analysis for Microarrays software ("SAM") was also used to identify a set of significant peaks. SAM is described in detail in Tusher V, et al., (2001). The results of the SAM analysis are presented in Table 18.

The identities of preferred biomarkers are determined using a combination of methods. For example, proteins in the fractions following the Hyper Q DF fractionation column are separated on an acrylamide gel and a band containing the biomarker is cut out of the gel. The protein in the band is destained. The gel is dried using acetonitrile and then subject to digestion in a solution of trypsin. The digest fragments are analyzed on a Ciphergen PBSII mass spectrometer. The determined masses are used to interrogate a protein database, which identify the protein as having the same tryptic digest pattern. All of these identifications are further confirmed by tandem MS analysis. Tables 7-17 present the average measured intensities for the various biomarkers under different conditions in tabular form. For example, Tables 7-10 show the average measured peak intensities observed for biomarkers with significant p values found in the first fraction eluted from the QHyper DF column. Specifically, Tables 7 and 8 show the peak intensities of biomarkers observed on the IMAC30 chip at low and high laser intensity readings, respectively. The term "no sig. cliff" is used to indicate that no significant differences were observed for the indicated set of comparisons. Note that each Table first includes three data sets corresponding to differences in biomarker intensity readings taken at particular time points as a function of patient status. The final three sets in each table, for which fewer significant peaks were observed, lists biomarkers from within the same patient group whose intensities changed significantly over time. In some cases, no significant biomarkers were identified using a particular set of subjects and assay conditions. For example, Table 7 shows that in fraction 1 of a QHyper DF fractionation of samples taken 2 hours after a treadmill exercise, no significant peak differences were observed between patient groups on the IMAC30 chip read at low intensity. Similarly, Table 7 shows that when Fraction 1 samples taken from any patient group immediately after and two hours after a treadmill exercise are analyzed on an IMAC30 chip at low intensity, the peak profiles obtained do not differ significantly from the profiles observed under the same conditions using samples taken before exercise.

Tables 9 and 10 summarize data obtained using the same samples, fraction and time points as Tables 7 and 8, except that the biomarker data was obtained by reading a CM10 chip at low and high laser intensity settings, respectively.

Tables 11, 12, 13 and 14 summarize data obtained using the same samples and time points as Tables 7, 8, 9 and 10, respectively, except that the biomarker peaks observed are those found in fraction 4 after QHyper DF fractionation.

Tables 15, 16 and 17 summarize data obtained using the same samples and time points as Tables 7, 8 and 9, respectively, except that the biomarker peaks are those found in fraction 6 after QHyper DF fractionation.

TABLE 7

Conditions: Fraction 1; IMAC30; Low Intensity

| | | Average Measured Peak Intensity | | |
|---|---|---|---|---|
| m/z | p value | Normal | LC | PAD |
| Significant Biomarker Intensity Changes Between Subject Groups | | | | |
| Pre-exercise | | | | |
| 5487.1 | 0.01295 | 16.91 | 26.70 | 11.44 |
| 14695.9 | 0.02513 | 5.04 | 4.70 | 6.63 |
| 54144.9 | 0.02647 | 1.31 | 1.80 | 1.40 |
| 6150.1 | 0.03564 | 6.70 | 11.22 | 7.98 |
| Immediately After Exercise | | | | |
| 5487.3 | 0.02322 | 26.20 | 22.90 | 13.61 |
| 6150.1 | 0.02360 | 17.10 | 14.53 | 11.00 |
| 2 hrs After Exercise | | | | |
| No sig. changes | — | — | — | — |
| Significant Biomarker Intensity Changes Within Subject Groups Over Time | | | | |
| No significant changes observed in biomarker intensity under these conditions | | | | |

TABLE 8

Conditions: Fraction 4; IMAC30; High Intensity

Significant Biomarker Intensity Changes Between Subject Groups

| | | Average Measured Peak Intensity | | |
|---|---|---|---|---|
| m/z | p value | Normal Pre-Dose | LC Pre-Dose | PAD Pre-Dose |
| Pre-exercise | | | | |
| 11973.9 Immediate | 0.02319 | 6.70 | 6.81 | 9.27 |
| 11973.9 2 hours | 0.02453 | 6.32 | 7.32 | 8.91 |
| 75053.2 | 0.00157 | 0.81 | 0.82 | 0.54 |
| 151061.2 | 0.01281 | 0.95 | 0.90 | 0.70 |
| 10378.0 (broad peak with 10.2 kD) | 0.03065 | 9.40 | 12.30 | 9.80 |
| 10194.1 | 0.04546 | 6.71 | 11.11 | 6.51 |

Significant Biomarker Intensity Changes Within Subject Groups Over Time

| | | Average Measured Peak Intensity | | |
|---|---|---|---|---|
| m/z | p value | Pre-exercise | Immediately After Exercise | 2 Hrs After Exercise |
| Normal | | | | |
| No. sig. changes LC | — | — | — | — |
| 75053.2 PAD | 0.04978 | 0.52 | 0.60 | 0.82 |
| No sig. changes | — | — | — | — |

TABLE 9

Conditions: Fraction 1; CM10; Low Intensity

Significant Biomarker Intensity Changes Between Subject Groups

| | | Average Measured Peak Intensity | | |
|---|---|---|---|---|
| m/z | p value | Normal | LC | PAD |
| Pre-exercise | | | | |
| 3026.4 | 0.01131 | 4.04 | 3.00 | 4.81 |
| 46927.5 | 0.03811 | 0.91 | 0.80 | 0.90 |
| Immediately After Exercise | | | | |
| 3026.4 | 0.01131 | 4.04 | 3.00 | 4.81 |
| 3026.4 2 hrs After Exercise | 0.01131 | 4.04 | 3.00 | 4.8 |
| 3026.4 | 0.01131 | 4.04 | 3.00 | 4.81 |

Significant Biomarker Intensity Changes Within Subject Groups Over Time

| | | Average Measured Peak Intensity | | |
|---|---|---|---|---|
| m/z | p value | Pre-exercise | Immediately After Exercise | 2 Hrs After Exercise |
| Normal | | | | |
| 3140.8 | 0.04234 | 4.97 | 5.90 | 6.50 |
| 3426.7 | 0.04870 | 7.30 | 8.40 | 8.60 |

TABLE 9-continued

Conditions: Fraction 1; CM10; Low Intensity

| | | | | |
|---|---|---|---|---|
| LC | | | | |
| 3140.8 | 0.04883 | 6.30 | 8.10 | 5.41 |
| PAD | | | | |
| No sig. changes | — | — | — | — |

TABLE 10

Conditions: Fraction 1; CM10; High Intensity

| | | Average Measured Peak Intensity | | |
|---|---|---|---|---|
| m/z | p value | Normal | LC | PAD |

Significant Biomarker Intensity Changes Between Subject Groups

Pre-exercise

| | | | | |
|---|---|---|---|---|
| 12043.6 | 0.00308 | 6.53 | 7.10 | 10.50 |
| 14058.1 | 0.03196 | 2.32 | 2.34 | 3.70 |
| 14942.6 | 0.03691 | 18.10 | 16.33 | 23.72 |

Immediately After Exercise

| | | | | |
|---|---|---|---|---|
| 15140.7 | 0.00706 | 7.10 | 5.97 | 9.22 |
| 23651.9 | 0.00859 | 10.10 | 10.41 | 15.60 |
| 12043.2 | 0.02272 | 7.10 | 7.14 | 10.32 |
| 14942.6 | 0.02544 | 18.20 | 15.84 | 22.90 |

2 hrs After Exercise

| | | | | |
|---|---|---|---|---|
| 11950.4 | 0.00784 | 7.10 | 5.97 | 9.20 |
| 14085.8 | 0.02693 | 2.30 | 2.64 | 3.80 |
| 14942.6 | 0.04414 | 18.60 | 14.36 | 23.90 |
| 15140.7 | 0.04937 | 7.31 | 5.61 | 8.71 |
| 23651.9 | 0.04939 | 9.40 | 10.40 | 13.50 |

Significant Biomarker Intensity Changes Within Subject Groups Over Time

No significant changes observed in biomarker intensity under these conditions

TABLE 11

Conditions: Fraction 4; IMAC30; Low Intensity

Significant Biomarker Intensity Changes Between Subject Groups

| | | Average Measured Peak Intensity | | |
|---|---|---|---|---|
| m/z | p value | Normal | LC | PAD |

Pre-exercise

| | | | | |
|---|---|---|---|---|
| 6197.9 | 0.0034 | 0.72 | 0.70 | 0.90 |
| 5875.5 | 0.0081 | 0.90 | 0.93 | 1.20 |
| 5028.4 | 0.0126 | 1.60 | 1.80 | 2.12 |
| 11718.3 | 0.030 | 0.52 | 0.74 | 0.93 |
| 94640.5 | 0.0356 | 0.14 | 0.10 | 0.20 |
| 5423.7 | 0.0484 | 1.10 | 1.10 | 1.40 |

Immediately After Exercise

| | | | | |
|---|---|---|---|---|
| 5028.4 | 0.0383 | 1.70 | 2.54 | 1.93 |
| 6635.0 | 0.0405 | 6.60 | 8.70 | 6.12 |

2 hrs After Exercise

| | | | | |
|---|---|---|---|---|
| 11718.9 | 0.0218 | 0.50 | 0.61 | 0.97 |

TABLE 11-continued

Conditions: Fraction 4; IMAC30; Low Intensity

Significant Biomarker Intensity Changes Within Subject Groups Over Time

| | | Average Measured Peak Intensity | | |
|---|---|---|---|---|
| m/z | p value | Pre-exercise | Immediately After Exercise | 2 Hrs After Exercise |

Normal

| | | | | |
|---|---|---|---|---|
| 22267.5 | 0.01364 | 0.63 | 0.74 | 0.93 |
| 5875.5 | 0.05468 | 0.90 | 0.90 | 1.10 |

LC

| | | | | |
|---|---|---|---|---|
| No sig. changes | — | — | — | — |

PAD

| | | | | |
|---|---|---|---|---|
| No sig. changes | — | — | — | — |

TABLE 12

Conditions: Fraction 4; IMAC30; High Intensity

Significant Biomarker Intensity Changes Between Subject Groups

| | | Average Measured Peak Intensity | | |
|---|---|---|---|---|
| m/z | p value | Normal | LC | PAD |

Pre-exercise

| | | | | |
|---|---|---|---|---|
| 11958.8 (also 11.7, 12.1, 12.2) | 0.00333 | 1.40 | 1.90 | 2.83 |
| 42279.0 | 0.02488 | 0.54 | 0.50 | 0.41 |

Immediately After Exercise

| | | | | |
|---|---|---|---|---|
| 13959.1 | 0.02496 | 11.30 | 15.70 | 11.80 |
| 11958.8 | 0.03394 | 1.50 | 2.50 | 2.70 |

2 hrs After Exercise

| | | | | |
|---|---|---|---|---|
| No. sig. changes | — | — | — | — |

Significant Biomarker Intensity Changes Within Subject Groups Over Time

| | | Average Measured Peak Intensity | | |
|---|---|---|---|---|
| m/z | p value | Pre-exercise | Immediately After Exercise | 2 Hrs After Exercise |

Normal

| | | | | |
|---|---|---|---|---|
| 34154.2 | 0.03150 | 2.81 | 3.02 | 3.42 |
| 66401.9 | 0.03523 | 24.40 | 26.42 | 30.40 |

LC

| | | | | |
|---|---|---|---|---|
| No sig. changes | — | — | — | — |

PAD

| | | | | |
|---|---|---|---|---|
| No sig. changes | — | — | — | — |

TABLE 13

Conditions: Fraction 4; CM10; Low Intensity

Significant Biomarker Intensity Changes Between Subject Groups

| | | Average Measured Peak Intensity | | |
|---|---|---|---|---|
| m/z | p value | Normal | LC | PAD |
| Pre-exercise | | | | |
| 66593.8 | 6.55E−04 | 15.33 | 15.23 | 18.40 |
| 42056.9 | 0.0063 | 0.50 | 0.50 | 0.40 |
| 4722.5 | 0.0096 | 2.11 | 2.23 | 1.73 |
| 83633.1 | 0.0304 | 0.73 | 0.73 | 0.54 |
| 13753.1 | 0.0307 | 5.80 | 7.20 | 5.30 |
| 4151.4 | 0.0331 | 2.30 | 1.80 | 2.01 |
| 5074.9 | 0.0331 | 1.52 | 1.50 | 1.23 |
| 59195.3 | 0.0331 | 0.91 | 0.91 | 1.10 |
| 4482.6 | 0.0467 | 1.73 | 1.84 | 1.50 |
| 4654.9 | 0.0468 | 1.20 | 0.93 | 1.10 |
| Immediately After Exercise | | | | |
| 13753.1 | 0.0211 | 5.40 | 7.60 | 5.50 |
| 2 hrs After Exercise | | | | |
| No sig. changes | — | — | — | — |

Significant Biomarker Intensity Changes Within Subject Groups Over Time

| | | Average Measured Peak Intensity | | |
|---|---|---|---|---|
| m/z | p value | Pre-exercise | Immediately After Exercise | 2 Hrs After Exercise |
| Normal | | | | |
| 44536.2 | 0.015 | 1.20 | 1.31 | 1.50 |
| 89098.9 | 0.0246 | 0.30 | 0.32 | 0.40 |
| 59195.3 | 0.0256 | 0.91 | 1.00 | 1.12 |
| 73315.3 | 0.0414 | 0.84 | 0.92 | 1.00 |
| 7933.9 | 0.0424 | 5.10 | 2.96 | 1.83 |
| LC | | | | |
| 28955.9 | 0.0435 | 3.22 | 3.60 | 2.80 |
| 5416.6 | 0.0498 | 1.23 | 1.50 | 1.20 |
| PAD | | | | |
| 49034.0 | 0.0173 | 0.13 | 0.11 | 0.12 |
| 4654.9 | 0.042 | 1.10 | 1.10 | 0.97 |

TABLE 14

Conditions: Fraction 4; CM10; High Intensity

Significant Biomarker Intensity Changes Between Subject Groups

| | | Average Measured Peak Intensity | | |
|---|---|---|---|---|
| m/z | p value | Normal | LC | PAD |
| Pre-exercise | | | | |
| 66469.3 | 7.98E−04 | 29.80 | 30.60 | 36.60 |
| 41994.6 | 0.00105 | 0.31 | 0.30 | 0.20 |
| 44441.2 | 0.00187 | 0.94 | 0.92 | 1.11 |
| 99848.7 | 0.00270 | 0.80 | 0.80 | 0.97 |
| 10834.9 | 0.00455 | 0.80 | 0.93 | 0.70 |
| 13924.3 | 0.00908 | 13.10 | 18.70 | 12.20 |
| 59116.5 | 0.00917 | 0.80 | 0.80 | 0.94 |
| 34271.8 | 0.00969 | 1.80 | 1.80 | 2.20 |
| 13272.4 | 0.01036 | 0.40 | 0.40 | 0.30 |
| 74864.3 | 0.01280 | 0.80 | 0.90 | 0.70 |
| Immediately After Exercise | | | | |
| 13924.3 | 0.00906 | 12.60 | 20.64 | 12.60 |
| 11204.5 | 0.02645 | 0.74 | 0.80 | 0.70 |
| 14043.1 | 0.03691 | 34.80 | 49.90 | 39.80 |
| 44441.2 | 0.04075 | 0.96 | 0.90 | 1.04 |
| 2 hrs After Exercise | | | | |
| 17374.4 | 0.02125 | 8.60 | 9.4 | 6.5 |
| 17374.4 | 0.02125 | 8.60 | 9.4 | 6.5 |

Significant Biomarker Intensity Changes Within Subject Groups Over Time

| | | Average Measured Peak Intensity | | |
|---|---|---|---|---|
| m/z | p value | Pre-exercise | Immediately After Exercise | 2 Hrs After Exercise |
| Normal | | | | |
| 66469.3 | 0.01625 | 29.80 | 32.96 | 36.44 |
| 83573.1 | 0.02272 | 0.70 | 0.51 | 0.40 |
| LC | | | | |
| 10834.9 | 0.04351 | 0.90 | 0.80 | 0.70 |
| 11272.6 | 0.05481 | 0.50 | 0.32 | 0.50 |
| PAD | | | | |
| 132875.3 | 0.03671 | 4.50 | 3.93 | 4.08 |
| 21137.1 | 0.03689 | 0.70 | 0.70 | 0.60 |

TABLE 15

Conditions: Fraction 6; IMAC30; Low Intensity

Significant Biomarker Intensity Changes Between Subject Groups

| | | Average Measured Peak Intensity | | |
|---|---|---|---|---|
| m/z | p value | Normal | LC | PAD |
| Pre-exercise | | | | |
| 6642.8 | 0.04238 | 17.60 | 23.50 | 15.14 |
| 8821.5 | 0.04572 | 13.31 | 10.90 | 11.13 |
| Immediately After Exercise | | | | |
| 6642.8 | 0.02960 | 16.44 | 23.70 | 17.90 |
| 13893.2 | 0.03105 | 5.90 | 7.99 | 5.80 |
| 2 hrs After Exercise | | | | |
| 6642.8 | 0.04100 | 16.40 | 22.40 | 14.03 |

Significant Biomarker Intensity Changes Within Subject Groups Over Time

| | | Average Measured Peak Intensity | | |
|---|---|---|---|---|
| m/z | p value | Pre-exercise | Immediately After Exercise | 2 Hrs After Exercise |
| Normal | | | | |
| No sig. changes | — | — | — | — |
| LC | | | | |
| No sig. changes | — | — | — | — |
| PAD | | | | |
| No sig. changes | — | — | — | — |

TABLE 16

Conditions: Fraction 6; IMAC30; High Intensity

Significant Biomarker Intensity Changes Between Subject Groups

| | | Average Measured Peak Intensity | | |
|---|---|---|---|---|
| m/z | p value | Normal | LC | PAD |
| Pre-exercise | | | | |
| 13720.2 | 0.01125 | 0.71 | 0.60 | 1.10 |
| 13720.2 | 0.01125 | 0.71 | 0.60 | 1.10 |
| Immediately After Exercise | | | | |
| No sig. changes | — | — | — | — |
| 2 hrs After Exercise | | | | |
| 14390.0 | 0.0244 | 44.03 | 38.31 | 37.98 |
| 14483.8 | 0.03737 | 26.44 | 23.04 | 22.60 |
| 28140.1 | 0.04133 | 75.10 | 64.20 | 64.10 |

Significant Biomarker Intensity Changes Within Subject Groups Over Time

| | | Average Measured Peak Intensity | | |
|---|---|---|---|---|
| m/z | p value | Pre-exercise | Immediately After Exercise | 2 Hrs After Exercise |
| Normal | | | | |
| No sig. changes | — | — | — | — |
| LC | | | | |
| 12814.4 | 0.0627 | 0.80 | 0.93 | 1.14 |
| PAD | | | | |
| 11544.6 | 0.02788 | 1.31 | 1.24 | 1.72 |
| 56032.7 | 0.02872 | 0.42 | 0.30 | 0.33 |
| 14811.7 | 0.04469 | 4.40 | 3.80 | 3.64 |

TABLE 17

Conditions: Fraction 6; CM10; High Intensity

Significant Biomarker Intensity Changes Between Subject Groups

| | | Average Measured Peak Intensity | | |
|---|---|---|---|---|
| m/z | p value | Normal | LC | PAD |
| Pre-exercise | | | | |
| 10131.44 | 0.02647 | 2.01 | 1.43 | 3.70 |
| Immediately After Exercise | | | | |
| 13983.7 | 0.02650 | 7.03 | 11.50 | 5.93 |
| 14104.0 | 0.02849 | 21.90 | 30.91 | 20.62 |
| 2 hrs After Exercise | | | | |
| 18183.9 | 0.00773 | 3.03 | 2.32 | 2.11 |
| 28994.6 | 0.01110 | 11.63 | 9.50 | 9.61 |
| 17741.7 | 0.01199 | 11.11 | 8.33 | 7.60 |
| 17541.8 | 0.02006 | 34.00 | 26.40 | 23.44 |
| 28107.7 | 0.02551 | 63.20 | 55.90 | 52.70 |
| 17416.5 | 0.03600 | 24.80 | 23.32 | 18.91 |

Significant Biomarker Intensity Changes Within Subject Groups Over Time

| | | Average Measured Peak Intensity | | |
|---|---|---|---|---|
| m/z | p value | Pre-exercise | Immediately After Exercise | 2 Hrs After Exercise |
| Normal | | | | |
| 94427.4 | 0.06495 | 0.20 | 0.23 | 0.30 |
| LC | | | | |
| No sig. changes | — | — | — | — |
| PAD | | | | |
| 45240.3 | 0.02186 | 0.92 | 0.90 | 0.80 |

TABLE 18

Peaks Found to be Significant by SAM (Significance Analysis of Microarrays)

| m/w | array | fraction | Identity | Characteristics |
|---|---|---|---|---|
| 11.9 kd | IMAC high | fxn 4 | | |
| 12 kd | cm10 high | fxn 1 | | |
| 13.9 kd | cm10 high | fxn 4 | Transthyretin | High in LC group; does not appear to change with exercise |
| 14.9 kd | cm10 high | fxn 1 | | |
| 42 kd | cm10 high | fxn 4 | fetuin | Low in PAD group at baseline; Normal group drops to PAD levels at time 2 hrs; LC group drops as well but not as dramatic |
| 44 kd | cm10 high | fxn 4 | albumin—triple charged albumin dimer | High in PAD group at baseline; Both normal and LC increase at time 2 hrs |
| 59 kd | cm10 high | fxn 4 | alpha 1B glycoprotein | High in PAD group at baseline; Both normal and LC increase at time 2 hrs |
| 66 kd | cm10 high | fxn 4 | albumin | High in PAD group at baseline; Normal group increases to PAD levels at time 2 hrs; LC increases but not as substantial |

TABLE 18-continued

Peaks Found to be Significant by SAM (Significance Analysis of Microarrays)

| m/w | array | fraction | Identity | Characteristics |
|---|---|---|---|---|
| 99 kd | cm 10 high | fxn 4 | | High in PAD group at baseline; Both normal and LC increase at time 2 hrs |
| 23 kd | cm 10 high | fxn 1 | kappa chain of IgG | |
| 34 kd | cm 10 high | fxn 4 | | |
| 4.7 kd | cm 10 low | fxn 4 | | |
| 94 kd | cm 10 high | fxn 6 | dimer of alpha1 antitrypsin | |

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method for qualifying peripheral artery disease (PAM) status in a subject comprising:
   a. measuring α1β glycoprotein from said subject; and
   b. correlating the measurement with PAD status.

2. The method of claim 1, wherein step (a) is carried out on a sample obtained from a subject prior to exercise.

3. The method of claim 1, further comprising measuring a second biomarker selected from the group consisting of albumin, fetuin, triple charge dieter of albumin, transthyretin, and dimer of α1-antitrypsin and correlating the measurement with PAD status.

4. The method of claim 1, further comprising measuring each of: albumin, fetuin, triple charge dimer of albumin, transthyretin, and dimer of α1-antitrypsin.

5. The method of claim 1, wherein α1β glycoprotein is measured by capturing the biomarker on an adsorbent surface of a SELDI probe and detecting the captured biomarkers by laser desorption-ionization mass spectrometry.

6. The method of claim 1, wherein α1β glycoprotein is measured by immunoassay.

7. The method of claim 1, wherein the sample is blood plasma.

8. The method claim 1, wherein the correlating is performed by a software classification algorithm.

9. The method of claim 1, wherein PAD status is selected from non-PAD, PAD, and long claudicator PAD.

10. A method for managing subject treatment based on PAD status, the method comprising qualifying a subject according to the method of claim 1, and managing subject treatment based on the status.

11. The method of claim 10, wherein PAD status is selected from non-PAD and PAD.

12. The method of claim 1, wherein PAD status is selected from non-PAD and long claudicator PAD.

13. The method claim 1, wherein PAD status is selected from PAD and long claudicator PAD.

14. The method of claim 5, wherein the adsorbent is a cation exchange adsorbent.

15. The method of claim 9, wherein, if the measurement correlates with PAD, then managing subject treatment comprises prescribing an exercise treatment regimen for the subject.

16. The method of claim 10, further comprising measuring the at least one additional biomarker after subject management.

17. A method for qualifying PAD status in a subject comprising the method of claim 1, wherein said subject is identified as having at least one symptom consistent with an increased likelihood that the subject will be afflicted with PAD.

18. A method for qualifying PAD status in a subject comprising the method of claim 17, wherein said subject is identified as having at least one condition selected from cigarette smoking, hyperlipidemia, hypertension and family history of peripheral artery disease.

* * * * *